United States Patent
Svetlichny et al.

(10) Patent No.: US 11,248,241 B2
(45) Date of Patent: *Feb. 15, 2022

(54) METHODS OF PRODUCING LACTIC ACID OR A SALT OR AN ESTER THEREOF BY USING A VERSATILE EXTREMELY THERMOPHILIC BACTERIA

(71) Applicant: Zhejiang Youcheng Holding Group Co., Ltd., Hangzhou (CN)

(72) Inventors: Vitaly Svetlichny, Cologne (DE); Simon Curvers, Cologne (DE)

(73) Assignee: HANGZOU DEHONG TECHNOLOGY CO., LTD., Hangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/271,674

(22) Filed: Feb. 8, 2019

(65) Prior Publication Data

US 2019/0169655 A1 Jun. 6, 2019

Related U.S. Application Data

(63) Continuation-in-part of application No. 15/232,438, filed on Aug. 9, 2016, now abandoned, which is a continuation of application No. 14/349,062, filed as application No. PCT/EP2012/069808 on Oct. 7, 2012, now abandoned.

(60) Provisional application No. 61/669,998, filed on Jul. 10, 2012, provisional application No. 61/556,448, filed on Nov. 7, 2011, provisional application No. 61/544,831, filed on Oct. 7, 2011.

(30) Foreign Application Priority Data

| Oct. 7, 2011 | (EP) | 11008155 |
| Nov. 7, 2011 | (EP) | 11008857 |
| Jul. 10, 2012 | (EP) | 12175684 |

(51) Int. Cl.

| C12P 7/06 | (2006.01) |
| C12P 7/14 | (2006.01) |
| C12P 7/56 | (2006.01) |
| C12R 1/01 | (2006.01) |
| C12P 7/10 | (2006.01) |
| C12N 1/20 | (2006.01) |
| C12P 7/54 | (2006.01) |

(52) U.S. Cl.
CPC ............. *C12P 7/065* (2013.01); *C12N 1/20* (2013.01); *C12N 1/205* (2021.05); *C12P 7/10* (2013.01); *C12P 7/14* (2013.01); *C12P 7/54* (2013.01); *C12P 7/56* (2013.01); *C12P 2201/00* (2013.01); *C12P 2203/00* (2013.01); *C12R 2001/01* (2021.05); *Y02E 50/10* (2013.01)

(58) Field of Classification Search
None
See application file for complete search history.

(56) References Cited

U.S. PATENT DOCUMENTS

| 6,555,350 | B2 | 4/2003 | Ahring et al. |
| 9,944,956 | B2* | 4/2018 | Curvers ............... C12P 7/56 |
| 2004/0253713 | A1 | 12/2004 | Green et al. |
| 2014/0370571 | A1 | 12/2014 | Svetlichnyi et al. |
| 2016/0340696 | A1 | 11/2016 | Svetlichnyi et al. |

FOREIGN PATENT DOCUMENTS

| WO | 2007/134607 A1 | 11/2007 |
| WO | 2010/014976 A2 | 2/2010 |
| WO | 2013/050582 A2 | 4/2013 |

OTHER PUBLICATIONS

Angelidaki et al. Appl. Microbiol. Biotechnol. (1990) 33: 469-472 (Year: 1990).*
Verbeke et al. "Isolates of Thermoanaerobacter thermohydrosulfuricus from decaying wood compost display genetic and phenotypic microdiversity," FEMS Microbiol Ecol, 2011, 78:473-487.
Pearson et al. "Improved tools for biological sequence comparison," Proc. Natl. Acad. Sci. USA, Apr. 1988, 85:2444-2448.
PCT/EP2012/069808 International Search Report dated May 7, 2013.
Balat. "Production of bioethanol from lignocellulosic materials via the biochemical pathway: A review," Energy Conversion and Management, 2011, 52:858-875.
"T.mathranii 16S rRNA gene," Database EMBL, Aug. 20, 1997 [retrieved from the Internet on Nov. 16, 2016], Database accession No. Y11279, XP002690368.
"Thermoanaerobacter thermohydrosulfuricus strain E100-69 16S ribosomal RNA gene," Partial sequence, EBI accession No. EM_STD:L09161, Jan. 7, 1994 [retrieved from the Internet on Nov. 16, 2016], XP002690370.

(Continued)

*Primary Examiner* — Susan M Hanley
(74) *Attorney, Agent, or Firm* — Wagenecht IP Law Group PC

(57) ABSTRACT

A method of producing lactic acid or a salt or an ester thereof, which includes incubating lignocellulosic hydrolysates in the presence of cells of an isolated strain of *Thermoanaerobactor* at a temperature above 70 degrees Celsius, wherein the *Thermoanaerobactor* comprises a 16S rDNA sequence at least 99% identical to the nucleic acid sequence selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, and SEQ ID NO. 8

16 Claims, 13 Drawing Sheets

Specification includes a Sequence Listing.

(56) References Cited

OTHER PUBLICATIONS

Larsen et al. "Thermoanaerobacter *Mathranii* sp. nov., an ethanol-producing, extremely thermophilic anaerobic bacterium from a hot spring in Iceland," Archives of Microbiology, Jan. 1, 1997, 168(2):114-119, Springer-Verlag, DE.

Lee et al. Taxonomic Distinction of Saccharolytic Thermophilic Anaerobes: Description of *Thermoanaerobacterium xytanolyticum* gen. nov., sp.. nov., and *Thermoanaerobacterium saccharolyticum* gen. nov., sp. nov.; Reclassification of Thermoanaerobium brockii, Clostridium thermosulfurogenes, and Clostridium thermohydrosulfuricum E100-69 as Thermoanaerobacter brockii comb, nov., Thermoanaerobacterium thermosulfurigenes comb. nov., and Thermoanaerobacter thermohydrosulfuricus comb. nov., Respectively; and Transfer of Clostridium Int. J. Systymatic Bactiol. (1993) 43(1): 41-51.

Rainey et al. "Phylogenetic Analysis of Anaerobic Thermophilic Bacteria: Aid for Their Reclassification," Journal of Bacteriology, American Society for Microbiology, Aug. 1, 1993, 175(15):4772-4779, Washington DC, US.

\* cited by examiner

FIGURE 2

**16SrDNA consensus sequence for *Thermoanaerobacter* sp. DIB004G (SEQ ID NO. 1)**

```
ggttgggtca ccggcttcgg gtgtcgcagg ctctcgtggt gtgacgggcg gtgtgtacaa     60
ggcccgggaa cgtattcacc gcggcatgct gatccgcgat tactagcgat tccgacttca    120
tgcaggcgag ttgcagcctg caatccgaac ttggaccggc tttttgggat tcgctccgcc    180
tcacggcttc gcttccctct gtaccggcca ttgtagcacg tgtgtggccc agggcattta    240
gggcatgatg atttgacgtc atccccacct tcctccgtgt cctccacggc agtccctcta    300
gagtgcccgg cttacccgct ggcaactaga ggcaggggtt gcgctcgttg cgggacttaa    360
cccaacatct cacgacacga gctgacgaca accatgcacc acctgtgcag gctccttacc    420
tcccggtaag gtcgctcccc tttcggttcg ctactacctg catgtcaagc cctggtaagg    480
ttcttcgcgt tgcttcgaat taaaccacat gctccaccgc ttgtgcgggc ccccgtcaat    540
tcctttgagt ttcaaccttg cggccgtact ccccaggcgg ggtacttatt gcgttcgcta    600
cggcacggaa cgcttccgcg ccccacacct agtacccatc gtttacagcg tggactacca    660
gggtatctaa tcctgttcgc tccccacgct ttcgcgcctc agcgtcaggg ccagtccaga    720
gagtcgcctt cgccactggt attcctcccg atatctacgc atttcaccgc tacaccggga    780
attccactcc cctctcctgc cctctagcca atcagtttca gatgctaccc cccggttgag    840
cccgggtctt ttacacctga cttgattgac cgcctacgcg ccctttacgc ccagtaattc    900
cggacaacgc tcgcccccta cgtcttaccg cggctgctgg cacgtagtta gccggggctt    960
tcgtgtggta ccgtcatccc ttcttcccac actaacgggg tttacaaccc gaaggccttc   1020
ctcccccacg cggcgtcgct gggtcaggct tccgccatt gcccaagatt ccccactgct    1080
gcctcccgta ggagtctggg ccgtgtctca gtcccagtgt ggccgtccac cctctcaggc   1140
cggctacccg tcgtcgcctt ggtaggccgt taccctacca actagctgat gggacgcggg   1200
cccatcctta agcggtagct tgcgcttccc tttcctccct ataggatgcc ctataaggag   1260
cttatccagt attaccaccc ctttcgaggt gctatcccgg tcttaagggt aggttgccca   1320
cgcgttactc accegtccgc cgctatccgc cacccaacta cgttgagtgc cggaccgctc   1380
gactgcatgt gttaggcacg ccgccagcgt tcgtcctgag cc                      1422
```

FIGURE 3

**16SrDNA consensus sequence for *Thermoanaerobacter* sp. DIB087G (SEQ ID NO. 2)**

```
ACTCAAGTGG GCACGTTTTT TTCTCTTCAT CACGTTTCTA ACATGCCCAC TTGAGTGCCG    60
GGTTGGGTCA CCGGCTTCGG GTGTTGCAGA CTCTCGTGGT GTGACGGGCG GTGTGTACAA   120
GGCCCGGGAA CGTATTCACC GCGGCATGCT GATCCGCGAT TACTAGCGAT TCCGACTTCA   180
TGCAGGCGAG TTGCAGCCTG CAATCCGAAC TTGGACCGGC TTTTTGGGGT CCGCTCCAGA   240
TCGCTCCTTC GCCTCCCTCT GTACCGGCCA TTGTAGCACG TGTGTGGCCC AGGGCATATA   300
GGGCATGATG ATTTGACGTC ATCCCCACCT TCCTCCGTGT TGTCCACGGC AGTCCCTCTA   360
GAGTGCCTCC GTCACTCAAC TGAACACGCT ATCCCTTCCT CTCTACTCTT TCCTAACATG   420
TTCAGTTGAG TGACGGACTG GCAACTAGAA GCAAGGGTTG CGCTCGTTGC GGGACTTAAC   480
CCAACATCTC ACGACACGAG CTGACGACAA CCATGCACCA CCTGTGCAGG CTCCCGGCAC   540
TCAAGTAGGC ACTTCATTCT CCCTCTTACT ACCTTCTCTA TCATGCCCAC TTGAGTGCCG   600
GGTCGCTCAC CTTTCGGCTC GCTACTACCT GCATGTCAAG CCCTGGTAAG GTTCTTCGCG   660
TTGCTTCGAA TTAAACCACA TGCTCCACCG CTTGTGCGGG CCCCCGTCAA TTCCTTTGAG   720
TTTCAACCTT GCGGCCGTAC TCCCCAGGCG GGGTACTTAT TGCGTTAACT ACGGCACGGA   780
ATGCTTCCGC ATCCCACACC TAGTACCCAT CGTTTACGGC GTGGACTACC AGGGTATCTA   840
ATCCTGTTTG CTCCCCACGC TTTCGCGCCT CAGCGTCAGG GTCAGTCCAG AGAGTCGCCT   900
TCGCCACTGG TATTCCTCCC GATATCTACG CATTTCACCG CTACACCGGG AATTCCACTC   960
CCCTCTCCTG CCCTCTAGCC ACCCAGTTTC ATGTGCATCC CCCGGGTTGA GCCCGGGTTT  1020
TTTACACCTG ACTTAAGTGG CCGCCTACGC GCCCTTTACG CCCAGTAATT CCGGACAACG  1080
CTCGCCCCCT ACGTCTTACC GCGGCTGCTG GCACGTAGTT AGCCGGGGCT TTCGTGTGGT  1140
ACCGTCATCT ATTCTTCCCA CACTATGAG CTTTACGACC CGAAGGCCTT CTTCGCTCAC  1200
GCGGCGTCGC TGCGTCAGGC TTTCGCCCAT TGCGCAAGAT TCCCCACTGC TGCCTCCCGT  1260
AGGAGTCTGG GCCGTGTCTC AGTCCCAGTG TGGCCGACCA CCCTCTCAGG CCGGCTACCC  1320
GTCGTCGCCT TGGTAGGCCG TTACCCTACC AACTAGCTGA TGGGACGCGG GCCCATCCTT  1380
AAGCGGTAGC TTCCGCTACC TTCCCTCCTC ATAGGATGCC CTACAAGGAG CTTATCCAGT  1440
ATTAGCACCC CTTTCGAGGT GTTATCCCGG TCTTAAGGGT AGGTTGCCCA CGCGTTACTC  1500
ACCCGTCCGC CGCTATCCGG CACTCAACTC CGTGCTTACC TTACTTTGCA CCACTTTTAT  1560
TACTTTCTTC TTCTACTATA CTTCCTTCCC CTTAAGTAAG CACTTAGTTG AGTGCCGGAC  1620
CGCTCGACTT GCATGTGTTA GGCACGCCGC CAGCGTTCG                          1660
```

FIGURE 4

**16SrDNA consensus sequence for *Thermoanaerobacter* sp. DIB097X (SEQ ID NO. 3)**

```
CCCGGTTGGG TCACCGGCTT CGGGTGTCGC AGGCTCTCGT GGTGTGACGG GCGGTGTGTA    60
CAAGGCCCGG GAACGTATTC ACCGCGGCAT GCTGATCCGC GATTACTAGC GATTCCGACT   120
TCATGCAGGC GAGTTGCAGC CTGCAATCCG AACTTGGACC GGCTTTTTGG GATTCGCTCC   180
GCCTCGCGGC TTCGCTCCCC TCTGTACCGG CCATTGTAGC ACGTGTGTGG CCCAGGGCAT   240
ATAGGGCATG ATGATTTGAC GTCATCCCCA CCTTCCTCCG TGTCCTCCAC GGCAGTCCCC   300
CTAGAGTGCC CGGCTTACCC GCTGGCAACT AGAGGCAGGG GTTGCGCTCG TTGCGGGACT   360
TAACCCAACA TCTCACGACA CGAGCTGACG ACAACCATGC ACCACCTGTG CAGGCTCCTT   420
ACCTCCCGGT AAGGTCGCTC CCCTTTCGGT TCGCTACTAC CTGCATGTCA AGCCCTGGTA   480
AGGTTCTTCG CGTTGCTTCG AATTAAACCA CATGCTCCAC CGCTTGTGCG GGCCCCCGTC   540
AATTCCTTTG AGTTTCAACC TTGCGGCCGT ACTCCCAGG CGGGGTACTT ATTGCGTTCG    600
CTACGGCACG GAACGCTTCC GCGCCCCACA CCTAGTACCC ATCGTTTACA GCGTGGACTA   660
CCAGGGTATC TAATCCTGTT CGCTCCCCAC GCTTTCGCGC CTCAGCGTCA GGGCCAGTCC   720
AGAGAGTCGC CTTCGCCACT GGTATTCCTC CCGATATCTA CGCATTTCAC CGCTACACCG   780
GGAATTCCAC TCCCCTCTCC TGCCCTCTAG CCAATCAGTT TCAGATGCTA CCCCCGGGTT   840
GAGCCCGGGT CTTTTACACC TGACTTGATT GACCGCCTAC GCGCCCTTTA CGCCCAGTAA   900
TTCCGGACAA CGCTCGCCCC CTACGTCTTA CCGCGGCTGC TGGCACGTAG TTAGCCGGGG   960
CTTTCGTGTG GTACCGTCAT CCCTTCTTCC CACACTAACG GGGTTTACAA CCCGAAGGCC  1020
TTCCTCCCCC ACGCGGCGTC GCTGGGTCAG GCTTCCGCCC ATTGCCCAAG ATTCCCCACT  1080
GCTGCCTCCC GTAGGAGTCT GGGCCGTGTC TCAGTCCCAG TGTGGCCGAC CACCCTCTCA  1140
GGCCGGCTAC CCGTCGTCGC CTTGGTAGGC CGTTACCCTA CCAACTAGCT GATGGGACGC  1200
GGGCCCATCC TTAAGCGGTA GCTTGCGCCT CCCTTTCCTC CCTATAGGAT GCCCTATAAG  1260
GAGCTTATCC AGTATTACCA CCCCTTTCGA GGTGCTATCC CGGTCTTAAG GGTAGGTTGC  1320
CCACGCGTTA CTCACCCGTC CGCCGCTATC CGCCACCCAA CTACGTTGAG TGCCGGACCG  1380
CTCGACTTGC ATGTGTTAGG CACGCCGCCA GCGTTCGTCC TGAGCCATGA TCAAAC      1436
```

FIGURE 5

**16SrDNA consensus sequence for *Thermoanaerobacter* sp. DIB101G (SEQ ID NO. 4)**

```
gctcaggacg aacgctggcg gcgtgcctaa cacatgcaag tcgagcggtc cggcactcaa     60
ctaagtgctt acttaagggg aaggaagtat agtagaagaa gaaggtaata aaagtgatgc    120
aaagtaaggt aagcacggag ttgagtgccg gatagcggcg gacgggtgag taacgcgtgg    180
gcaacctacc cttaagaccg ggataacacc tcgaaagggg tgctaatact ggataagctc    240
cttgtagggc atcctatgag gagggaaggt agcggaagct accgcttaag gatgggcccg    300
cgtcccatca gctagttggt agggtaacgg cctaccaagg cgacgacggg tagccggcct    360
gagagggtgg tcggccacac tgggactgag acacggccca gactcctacg ggaggcagca    420
gtggggaatc ttgcgcaatg ggcgaaagcc tgacgcagcg acgccgcgtg agcgaagaag    480
gccttcgggt cgtaaagctc gatagtgtgg gaagaataga tgacggtacc acacgaaagc    540
cccggctaac tacgtgccag cagccgcggt aagacgtagg gggcgagcgt tgtccggaat    600
tactgggcgt aaagggcgcg taggcggcca cttaagtcag gtgtaaaaaa cccgggctca    660
acccggggga tgcacatgaa actgggtggc tagagggcag gagaggggag tggaattccc    720
ggtgtagcgg tgaaatgcgt agatatcggg aggaatacca gtggcgaagg cgactctctg    780
gactgaccct gacgctgagg cgcgaaagcg tggggagcaa acaggattag atacccggt     840
agtccacgcc gtaaacgatg ggtactaggt gtgggatgcg gaagcattcc gtgccgtagt    900
taacgcaata agtaccccgc ctggggagta cggccgcaag gttgaaactc aaaggaattg    960
acggggggccc gcacaagcgg tggagcatgt ggtttaattc gaagcaacgc gaagaacctt   1020
accagggctt gacatgcagg tagtagcgag ccgaaaggtg agcgacccgg cactcaagtg   1080
```

FIGURE 6

**16SrDNA consensus sequence for *Thermoanaerobacter* sp. DIB101X (SEQ ID NO. 5)**

```
GCCCCACTTT CGACGGCTCC CTCCTTCCCG GTTGGGTCAC CGGCTTCGGG TGTCGCAGGC    60
TCTCGTGGTG TGACGGGCGG TGTGTACAAG GCCCGGGAAC GTATTCACCG CGGCATGCTG   120
ATCCGCGATT ACTAGCGATT CCGACTTCAT GCAGGCGAGT TGCAGCCTGC AATCCGAACT   180
TGGACCGGCT TTTTGGGATT CGCTCCGCCT CGCGGCTTCG CTTCCCTCTG TACCGGCCAT   240
TGTAGCACGT GTGTGGCCCA GGGCATATAG GCATGATGA TTTGACGTCA TCCCCACCTT    300
CCTCCGTGTC CTCCACGGCA GTCCCTCTAG AGTGCCCGGC TTACCCGCTG GCAACTAGAG   360
GCAGGGGTTG CGCTCGTTGC GGGACTTAAC CCAACATCTC ACGACACGAG CTGACGACAA   420
CCATGCACCA CCTGTGCAGG CTCCTTACCT CCCGGTAAGG TCGCTCCCCT TTCGGTTCGC   480
TACTACCTGC ATGTCAAGCC CTGGTAAGGT TCTTCGCGTT GCTTCGAATT AAACCACATG   540
CTCCACCGCT TGTGCGGGCC CCCGTCAATT CCTTTGAGTT TCAACCTTGC GGCCGTACTC   600
CCCAGGCGGG GTACTTATTG CGTTCGCTAC GGCACGGAAC GCTTCCGCGC CCCACACCTA   660
GTACCCATCG TTTACAGCGT GGACTACCAG GGTATCTAAT CCTGTTCGCT CCCCACGCTT   720
TCGCGCCTCA GCGTCAGGGC CAGTCCAGAG AGTCGCCTTC GCCACTGGTA TTCCTCCCGA   780
TATCTACGCA TTTCACCGCT ACACCGGGAA TTCCACTCCC CTCTCCTGCC CTCTAGCCAA   840
TCAGTTTCAG ATGCTACCCC CGGGTTGAGC CCGGGTCTTT TACACCTGAC TTGATTGACC   900
GCCTACGCGC CCTTTACGCC CAGTAATTCC GGACAACGCT CGCCCCTAC GTCTTACCGC    960
GGCTGCTGGC ACGTAGTTAG CCGGGGCTTT CGTGTGGTAC CGTCATCCCT TCTTCCCACA  1020
CTAACGGGGT TTACAACCCG AAGGCCTTCC TCCCCACGC GGCGTCGCTG GGTCAGGCTT   1080
CCGCCCATTG CCCAAGATTC CCCACTGCTG CCTCCCGTAG GAGTCTGGGC CGTGTCTCAG  1140
TCCCAGTGTG GCCGACCACC CTCTCAGGCC GGCTACCCGT CGTCGCCTTG GTAGGCCGTT  1200
ACCCTACCAA CTAGCTGATG GGACGCGGGC CCATCCTTAA GCGGTAGCTT GCGCCTCCCT  1260
TTCCTCCCTA TAGGATGCCC TATAAGGAGC TTATCCAGTA TTACCACCCC TTTCGAGGTG  1320
CTATCCCGGT CTTAAGGGTA GGTTGCCCAC GCGTTACTCA CCCGTCCGCC GCTATCCGCC  1380
ACCCAACTAC GTTGAGTGCC GGACCGCTCG ACTTGCATGT GTTAGGCACG CCGCCAGCGT  1440
TCGTCCTGAG C                                                      1451
```

FIGURE 7

**16SrDNA consensus sequence for *Thermoanaerobacter* sp. DIB103X (SEQ ID NO. 6)**

```
TTCACCCCAA TCACCTGCCC CACCTTCGAC GGCTCCCTCC TCCCCGGTTG GGTCACCGGC    60
TTCGGGTGTC GCAGGCTCTC GTGGTGTGAC GGGCGGTGTG TACAAGGCCC GGGAACGTAT   120
TCACCGCGGC ATGCTGATCC GCGATTACTA GCGATTCCGA CTTCATGCAG GCGAGTTGCA   180
GCCTGCAATC CGAACTTGGA CCGGCTTTTT GGGATTCGCT CCGCCTCGCG GCTTCGCTCC   240
CCTCTGTACC GGCCATTGTA GCACGTGTGT GGCCCAGGGC ATATAGGGCA TGATGATTTG   300
ACGTCATCCC CACCTTCCTC CGTGTCCTCC ACGGCAGTCC CCTAGAGTG CCCGGCTTAC    360
CCGCTGGCAA CTAGAGGCAG GGGTTGCGCT CGTTGCGGGA CTTAACCCAA CATCTCACGA   420
CACGAGCTGA CGACAACCAT GCACCACCTG TGCAGGCTCC TTACCTCCCG GTAAGGTCGC   480
TCCCCTTTCG GTTCGCTACT ACCTGCATGT CAAGCCCTGG TAAGGTTCTT CGCGTTGCTT   540
CGAATTAAAC CACATGCTCC ACCGCTTGTG CGGGCCCCG TCAATTCCTT TGAGTTTCAA    600
CCTTGCGGCC GTACTCCCCA GGCGGGGTAC TTATTGCGTT CGCTACGGCA CGGAACGCTT   660
CCGCGCCCCA CACCTAGTAC CCATCGTTTA CAGCGTGGAC TACCAGGGTA TCTAATCCTG   720
TTCGCTCCCC ACGCTTTCGC GCCTCAGCGT CAGGGCCAGT CCAGAGAGTC GCCTTCGCCA   780
CTGGTATTCC TCCCGATATC TACGCATTTC ACCGCTACAC CGGGAATTCC ACTCCCCTCT   840
CCTGCCCTCT AGCCAATCAG TTTCAGATGC TACCCCCGGG TTGAGCCCGG GTCTTTTACA   900
CCTGACTTGA TTGACCGCCT ACGCGCCCTT TACGCCCAGT AATTCCGGAC AACGCTCGCC   960
CCCTACGTCT TACCGCGGCT GCTGGCACGT AGTTAGCCGG GGCTTTCGTG TGGTACCGTC  1020
ATCCCTTCTT CCCACACTAA CGGGGTTTAC AACCCGAAGG CCTTCCTCCC CCACGCGGCG  1080
TCGCTGGGTC AGGCTTCCGC CCATTGCCCA AGATTCCCCA CTGCTGCCTC CCGTAGGAGT  1140
CTGGGCCGTG TCTCAGTCCC AGTGTGGCCG ACCACCCTCT CAGGCCGGCT ACCCGTCGTC  1200
GCCTTGGTAG GCCGTTACCC TACCAACTAG CTGATGGGAC GCGGGCCCAT CCTTAAGCGG  1260
TAGCTTGCGC CTCCCTTTCC TCCCTATAGG ATGCCCTATA AGGAGCTTAT CCAGTATTAC  1320
CACCCCTTTC GAGGTGCTAT CCCGGTCTTA AGGGTAGGTT GCCCACGCGT TACTCACCCG  1480
TCCGCCGCTA TCCGCCACCC AACTACGTTG AGTGCCGGAC CGCTCGACTT GCATGTGTTA  1540
GGCACGCCGC CAGCGTTCGT CCTGA                                        1565
```

FIGURE 8

**16SrDNA consensus sequence for *Thermoanaerobacter* sp. DIB104X (SEQ ID NO. 7)**

```
ACTCAAGTGG GCACGTTTTT TTCTCTTCAT CACGTTTCTA ACATGCCCAC TTGAGTGCCG     60
GGTTGGGTCA CCGGCTTCGG GTGTTGCAGA CTCTCGTGGT GTGACGGGCG GTGTGTACAA    120
GGCCCGGGAA CGTATTCACC GCGGCATGCT GATCCGCGAT TACTAGCGAT TCCGACTTCA    180
TGCAGGCGAG TTGCAGCCTG CAATCCGAAC TTGGACCGGC TTTTTGGGGT CCGCTCCAGA    240
TCGCTCCTTC GCCTCCCTCT GTACCGGCCA TTGTAGCACG TGTGTGGCCC AGGGCATATA    300
GGGCATGATG ATTTGACGTC ATCCCCACCT TCCTCCGTGT TGTCCACGGC AGTCCCTCTA    360
GAGTGCCTCC GTCACTCAAC TGAACACGCT ATCCCTTCCT CTCTACTCTT TCCTAACATG    420
TTCAGTTGAG TGACGGACTG GCAACTAGAA GCAAGGGTTG CGCTCGTTGC GGGACTTAAC    480
CCAACATCTC ACGACACGAG CTGACGACAA CCATGCACCA CCTGTGCAGG CTCCCGGCAC    540
TCAAGTAGGC ACTTCATTCT CCCTCTTACT ACCTTCTCTA TCATGCCCAC TTGAGTGCCG    600
GGTCGCTCAC CTTTCGGCTC GCTACTACCT GCATGTCAAG CCCTGGTAAG GTTCTTCGCG    660
TTGCTTCGAA TTAAACCACA TGCTCCACCG CTTGTGCGGG CCCCCGTCAA TTCCTTTGAG    720
TTTCAACCTT GCGGCCGTAC TCCCCAGGCG GGGTACTTAT TGCGTTAACT ACGGCACGGA    780
ATGCTTCCGC ATCCCACACC TAGTACCCAT CGTTTACGGC GTGGACTACC AGGGTATCTA    840
ATCCTGTTTG CTCCCCACGC TTTCGCGCCT CAGCGTCAGG GTCAGTCCAG AGAGTCGCCT    900
TCGCCACTGG TATTCCTCCC GATATCTACG CATTTCACCG CTACACCGGG AATTCCACTC    960
CCCTCTCCTG CCCTCTAGCC ACCCAGTTTC ATGTGCATCC CCCGGGTTGA GCCCGGGTTT   1020
TTTACACCTG ACTTAAGTGG CCGCCTACGC GCCCTTTACG CCCAGTAATT CCGGACAACG   1080
CTCGCCCCCT ACGTCTTACC GCGGCTGCTG GCACGTAGTT AGCCGGGGCT TTCGTGTGGT   1140
ACCGTCATCT ATTCTTCCCA CACTATCGAG CTTTACGACC CGAAGGCCTT CTTCGCTCAC   1200
GCGGCGTCGC TGCGTCAGGC TTTCGCCCAT TGCGCAAGAT TCCCCACTGC TGCCTCCCGT   1260
AGGAGTCTGG GCCGTGTCTC AGTCCCAGTG TGGCCGACCA CCCTCTCAGG CCGGCTACCC   1320
GTCGTCGCCT TGGTAGGCCG TTACCCTACC AACTAGCTGA TGGGACGCGG GCCCATCCTT   1380
AAGCGGTAGC TTCCGCTACC TTCCCTCCTC ATAGGATGCC CTACAAGGAG CTTATCCAGT   1440
ATTAGCACCC CTTTCGAGGT GTTATCCCGG TCTTAAGGGT AGGTTGCCCA CGCGTTACTC   1500
ACCCGTCCGC CGCTATCCGG CACTCAACTC CGTGCTTACC TTACTTTGCA CCACTTTTAT   1560
TACTTTCTTC TTCTACTATA CTTCCTTCCC CTTAAGTAAG CACTTAGTTG AGTGCCGGAC   1620
CGCTCGACTT GCATGTGTTA GGCACGCCGC CAGCGTTCGT CCTGA                    1665
```

FIGURE 9

**16SrDNA consensus sequence for *Thermoanaerobacter* sp. DIB107X (SEQ ID NO. 8)**

```
TCAGGACGAA CGCTGGCGGC GTGCCTAACA CATGCAAGTC GAGCGGTCCG GCACTCAACG      60
TAGTTGAGTG GCGGATAGCG GCGGACGGGT GAGTAACGCG TGGGCAACCT ACCCTTAAGA     120
CCGGGATAGC ACCTCGAAAG GGGTGGTAAT ACTGGATAAG CTCCTTATAG GGCATCCTAT     180
AGGGAGGAAA GGGAAGCGCA AGCTACCGCT TAAGGATGGG CCCGCGTCCC ATCAGCTAGT     240
TGGTAGGGTA ACGGCCTACC AAGGCKACGA CGGGTAGCCG GCCTGAGAGG GTGGTCGGCC     300
ACACTGGGAC TGAGACACGG CCCAGACTCC TACGGGAGGC AGCAGTGGGG AATCTTGGGC     360
AATGGGCGGA AGCCTGACCC AGCGACGCCG CGTGGGGGAG GAAGGCCTTC GGGTTGTAAA     420
CCCCGTTAGT GTGGGAAGAA GGGATGACGG TACCACACGA AAGCCCCGGC TAACTACGTG     480
CCAGCAGCCG CGGTAAGACG TAGGGGGCGA GCGTTGTCCG GAATTACTGG GCGTAAAGGG     540
CGCGTAGGCG GTCAATCAAG TCAGGTGTAA AAGACCCGGG CTCAACCCGG GGGTAGCACC     600
TGAAACTGGT TGGCTAGAGG GCAGGAGAGG GGAGTGGAAT TCCCGGTGTA GCGGTGAAAT     660
GCGTAGATAT CGGGAGGAAT ACCAGTGGCG AAGGCGACTC TCTGGACTGG CCCTGACGCT     720
GAGGCGCGAA AGCGTGGGGA GCGAACAGGA TTAGATACCC TGGTAGTCCA CGCTGTAAAC     780
GATGGGTACT AGGTGTGGGG CGCGGAAGCG TTCCGTGCCG TAGCGAACGC AATAAGTACC     840
CCGCCTGGGG AGTACGGCCG CAAGGTTGAA ACTCAAAGGA ATTGACGGGG GCCCGCACAA     900
GCGGTGGAGC ATGTGGTTTA ATTCGAAGCA ACGCGAAGAA CCTTACCAGG GCTTGACATG     960
CAGGTGGTAG CGAACCGAAA GGTGAGCGAC CTTACCGGGA GGTAAGGAGC CTGCACAGGT    1020
GGTGCATGGT TGTCGTCAGC TCGTGTCGTG AGATGTTGGG TTAAGTCCCG CAACGAGCGC    1080
AACCCCTGCC TCTAGTTGCC AGCGG                                         1105
```

FIGURE 10

| Strain | Substrate | Ethanol | Acetate | Lactate | Ethanol:Acetate:Lactate |
|---|---|---|---|---|---|
| | | mM | mM | mM | mM:mM:mM |
| DIB004G | Cellobiose (25 mM gluc. equiv.) | 21,60 | 2,41 | 17,09 | 1 : 0,1 : 0,8 |
| | Glucose (25 mM) | 23,24 | 0,66 | 17,92 | 1 : 0,03 : 0,8 |
| | Xylan (31 mM xylose equiv.) | no growth | | | |
| | Xylose (30 mM) | 17,05 | 0,00 | 10,27 | 1 : 0,00 : 0,6 |
| DIB087G | Cellobiose (25 mM gluc. equiv.) | 6,75 | 9,55 | 25,75 | 1 : 1,4 : 3,8 |
| | Glucose (25 mM) | 1,16 | 4,20 | 23,82 | 1 : 3,6 : 20,6 |
| | Xylan (31 mM xylose equiv.) | no growth | | | |
| | Xylose (30 mM) | 2,91 | 5,84 | 17,52 | 1 : 2,0 : 6,0 |
| DIB097X | Cellobiose (25 mM gluc. equiv.) | 29,81 | 5,30 | 8,85 | 1 : 0,2 : 0,3 |
| | Glucose (25 mM) | 31,71 | 2,77 | 11,91 | 1 : 0,1 : 0,4 |
| | Xylan (31 mM xylose equiv.) | 19,83 | 8,95 | 5,10 | 1 : 0,5 : 0,3 |
| | Xylose (30 mM) | 25,46 | 1,07 | 8,16 | 1 : 0,04 : 0,3 |
| DIB101G | Cellobiose (25 mM gluc. equiv.) | 15,36 | 1,80 | 9,28 | 1 : 0,1 : 0,6 |
| | Glucose (25 mM) | 16,30 | 0,50 | 12,23 | 1 : 0,03 : 0,8 |
| | Xylan (31 mM xylose equiv.) | no growth | | | |
| | Xylose (30 mM) | 15,42 | 0,80 | 9,10 | 1 : 0,05 : 0,6 |
| DIB101X | Cellobiose (25 mM gluc. equiv.) | 12,31 | 2,70 | 6,70 | 1 : 0,2 : 0,5 |
| | Glucose (25 mM) | 9,20 | 3,75 | 9,27 | 1 : 0,4 : 1,0 |
| | Xylan (31 mM xylose equiv.) | 23,34 | 6,57 | 3,15 | 1 : 0,3 : 0,1 |
| | Xylose (30 mM) | 19,80 | 3,89 | 6,93 | 1 : 0,2 : 0,4 |
| DIB103X | Cellobiose (25 mM gluc. equiv.) | 36,67 | 6,60 | 9,90 | 1 : 0,2 : 0,3 |
| | Glucose (25 mM) | 29,24 | 0,65 | 7,77 | 1 : 0,02 : 0,3 |
| | Xylan (31 mM xylose equiv.) | 29,36 | 6,73 | 2,83 | 1 : 0,3 : 0,1 |
| | Xylose (30 mM) | 25,52 | 3,82 | 6,29 | 1 : 0,2 : 0,3 |
| DIB104X | Cellobiose (25 mM gluc. equiv.) | 18,54 | 4,89 | 19,11 | 1 : 0,3 : 1,0 |
| | Glucose (25 mM) | 6,71 | 3,25 | 23,21 | 1 : 0,5 : 3,5 |
| | Xylan (31 mM xylose equiv.) | no data | | | |
| | Xylose (30 mM) | 13,53 | 5,73 | 14,17 | 1 : 0,4 : 1,1 |
| DIB107X | Cellobiose (25 mM gluc. equiv.) | 35,87 | 4,74 | 12,12 | 1 : 0,1 : 0,3 |
| | Glucose (25 mM) | 21,96 | 1,93 | 15,10 | 1 : 0,1 : 0,7 |
| | Xylan (31 mM xylose equiv.) | 24,49 | 6,14 | 2,30 | 1 : 0,3 : 0,1 |
| | Xylose (30 mM) | 28,74 | 4,74 | 8,49 | 1 : 0,2 : 0,3 |
| T. mathranii DSM11426 | Cellobiose (25 mM gluc. equiv.) | 12,39 | 7,21 | 18,68 | 1 : 0,6 : 1,5 |
| | Glucose (25 mM) | 17,17 | 8,54 | 16,95 | 1 : 0,5 : 1,0 |
| | Xylan (31 mM xylose equiv.) | 19,94 | 4,86 | 2,72 | 1 : 0,2 : 0,1 |
| | Xylose (30 mM) | 13,66 | 4,86 | 12,60 | 1 : 0,4 : 0,9 |

All cultures were grown in sealed vessels at 72 °C for 6 days without agitation

FIGURE 11

| Culture | Substrate | Fermentation products | | | | Total products | Ethanol yield |
|---|---|---|---|---|---|---|---|
| | | Ethanol | Acetate | Lactate | Ethanol:Acetate:Lactate | | |
| | g /l (dry weight) | mM | mM | mM | mM:mM:mM | mM | mol% |
| DIB097X | poplar (20 g/l) | 13,1 | 7,4 | 4,3 | 1 : 0,56 : 0,33 | 24,8 | 52,82 |
| DIB087G | | 0,73 | 4,73 | 4,62 | 1 : 6,52 : 6,36 | 10,08 | 7,24 |
| DIB097X | | 13,1 | 7,4 | 4,3 | 1 : 0,56 : 0,33 | 24,8 | 52,82 |
| DIB101X | | 14,4 | 6,3 | 4,3 | 1 : 0,44 : 0,30 | 25,0 | 57,60 |
| DIB103X | | 8,51 | 8,15 | 6,07 | 1 : 0,96 : 0,71 | 22,7 | 37,44 |
| DIB104X | | 3,79 | 11,08 | 7,04 | 1 : 2,92 : 1,86 | 21,9 | 17,30 |
| DIB107X | | 8,57 | 7,39 | 3,35 | 1 : 0,86 : 0,39 | 19,3 | 44,38 |
| DSM11426 | | 7,8 | 5,7 | 3,3 | 1 : 0,73 : 0,42 | 16,8 | 46,43 |
| DIB004G | poplar (10 g/l) | 4,33 | 4,42 | 2,95 | 1 : 1,0 : 0,7 | 11,70 | 37,01 |
| DIB097X | | 5,12 | 4,28 | 0,00 | 1 : 0,8 : 0,0 | 9,40 | 54,47 |
| DIB004G | miscanthus (10 g/l) | 4,96 | 6,94 | 3,36 | 1 : 1,4 : 0,7 | 15,26 | 32,50 |
| DIB097X | | 7,17 | 7,72 | 0,00 | 1 : 1,1 : 0,0 | 14,89 | 48,15 |
| DIB004G | sugarcane bagasse (10 g/l) | 5,49 | 10,38 | 7,35 | 1 : 1,9 : 1,3 | 23,22 | 23,64 |
| DIB097X | | 12,76 | 8,24 | 3,19 | 1 : 0,7 : 0,3 | 24,19 | 52,75 |
| DIB004G | wheat straw (10 g/l) | 5,18 | 4,36 | 3,16 | 1 : 0,8 : 0,6 | 12,70 | 40,79 |
| DIB097X | | 8,02 | 5,55 | 0,00 | 1 : 0,7 : 0,0 | 13,57 | 59,10 |
| DIB004G | corn stalks (10 g/l) | 5,04 | 6,95 | 3,42 | 1 : 1,4 : 0,7 | 15,41 | 32,71 |
| DIB097X | | 9,23 | 7,28 | 0,00 | 1 : 0,8 : 0,0 | 16,51 | 55,91 |
| DIB004G | DDGS (10 g/l) | 9,61 | 4,27 | 2,51 | 1 : 0,4 : 0,3 | 16,39 | 58,63 |
| DIB097X | | 10,95 | 4,57 | 1,85 | 1 : 0,4 : 0,2 | 17,37 | 63,04 |
| DIB004G | untreated waste-paper (10 g/l) | 2,63 | 2,53 | 2,86 | 1 : 1,0 : 1,1 | 8,02 | 32,79 |
| DIB097X | | 2,24 | 2,85 | 0,00 | 1 : 1,3 : 0,0 | 5,09 | 44,01 |

All cultures were grown in sealed vessels at 72 °C for 6 days with shaking at 100 rpm

**Fermentation of *Thermoanaerobacter* sp. DIB097X on pretreated miscanthus grass**

**Fermentation of *Thermoanaerobacter* sp. DIB004G on non-pretreated ground corn seed**

METHODS OF PRODUCING LACTIC ACID OR A SALT OR AN ESTER THEREOF BY USING A VERSATILE EXTREMELY THERMOPHILIC BACTERIA

CROSS REFERENCE TO RELATED APPLICATIONS

This is a continuation-in-part of U.S. patent application Ser. No. 15/232,438, filed Aug. 9, 2016, which is a continuation of U.S. patent application Ser. No. 14/349,062, now abandoned, which is the US national phase entry of PCT/EP2012/069808, filed Oct. 7, 2012, which claims benefit of priority to U.S. provisional patent application No. 61/544,831, filed Oct. 7, 2011, European patent application no. 11008155.1, filed Oct. 7, 2011, US provisional patent application no. 61/556,448, filed Nov. 7, 2011, European patent application no. 11008857.2, filed Nov. 7, 2011, U.S. provisional patent application No. 61/669,998, filed Jul. 10, 2012, and European patent application no. 12175684.5, filed Jul. 10, 2012. The entire content of each is herein incorporated by reference its entirety.

INCORPORATION BY REFERENCE OF MATERIAL SUBMITTED IN A SEQUENCE LISTING

The official copy of the sequence listing is submitted electronically via EFS-Web as an ASCII formatted sequence listing with file "US14349062_CON_SEQID" created on 9 Aug. 2016 and having a size of 17 Kilobytes. The sequence listing contained in this ASCII formatted document forms part of the specification and is herein incorporated by reference in its entirety.

FIELD OF THE INVENTION

The invention pertains to methods of producing lactic acid or a salt or an ester thereof, the method comprising incubating lignocellulosic hydrolysates in the presence of cells of an isolated strain of *Thermoanaerobactor* at a temperature above 70 degrees Celsius.

BACKGROUND

In general, fermentation products are produced by degradation of starch-containing material into fermentable sugars by liquefaction and saccharification followed by conversion of the sugars directly or indirectly into the desired fermentation product using a fermenting organism.

However, the industry of producing fermentation products such as ethanol and lactic acid is facing the challenge of redirecting the production process from fermentation of relatively easily convertible but expensive starchy materials, to the complex but inexpensive lignocellulosic biomass such as plant biomass.

Unlike starch, which contains homogenous and easily hydrolyzed polymers, lignocellulosic biomass contains variable amounts of cellulose, hemicellulose, lignin and small amounts of protein, pectin, wax and other organic compounds. Lignocellulosic biomass should be understood in its broadest sense, so that it apart from wood, agricultural residues, energy crops also comprises different types of waste from both industry and households. Cellulosic biomass is a vast poorly exploited resource, and in some cases a waste problem. However, hexoses from cellulose can be converted by yeast to fuel ethanol for which there is a growing demand. Pentoses from hemicellulose cannot yet be converted to ethanol commercially but several promising ethanologenic microorganisms with the capacity to convert pentoses and hexoses are under development.

Typically, the first step in utilization of lignocellulosic biomass is a pretreatment step, in order to fractionate the components of lignocellulosic material and increase their surface area. The pretreatment method most often used is steam pretreatment, a process comprising heating of the lignocellulosic material by steam injection to a temperature of 130-230° C. Prior to or during steam pretreatment, a catalyst like mineral or organic acid or a caustic agent facilitating disintegration of the biomass structure can be added optionally.

Another type of lignocellulose hydrolysis is acid hydrolysis, where the lignocellulosic material is subjected to an acid such as sulphuric acid whereby the sugar polymers cellulose and hemicellulose are partly or completely hydrolysed to their constituent sugar monomers and the structure of the biomass is destroyed facilitating access of hydrolytic enzymes in subsequent processing steps.

A further method is wet oxidation wherein the material is treated with oxygen at 150-185° C. Either pretreatment can be followed by enzymatic hydrolysis to complete the release of sugar monomers. This pre-treatment step results in the hydrolysis of cellulose into glucose while hemicellulose is transformed into the pentoses xylose and arabinose and the hexoses glucose, mannose and galactose. Thus, in contrast to starch, the hydrolysis of lignocellulosic biomass results in the release of pentose sugars in addition to hexose sugars. This implies that useful fermenting organisms need to be able to convert both hexose and pentose sugars to desired fermentation products such as ethanol.

After the pre-treatment the lignocellulosic biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g. glucose, mannose, and galactose); and (4) the fermentation of pentose sugars (e.g., xylose and arabinose).

Each processing step can make the overall process more costly and, therefore, decrease the economic feasibility of producing biofuel or carbon-based chemicals from cellulosic biological material. Thus, there is a need to develop methods that reduce the number of processing steps needed to convert cellulosic biological material to biofuel and other commercially desirable materials.

The four biologically mediated transformations may occur in a single step in a process configuration called consolidated bioprocessing (CBP), which is distinguished from other less highly integrated configurations in that CBP does not involve a dedicated process step for cellulase and/or hemicellulase production. CBP offers the potential for higher efficiency than a processes requiring dedicated cellulase production in a distinct unit operation.

Therefore, the availability of novel microorganisms and methods for converting lignocellulosic biomass material to carbon-based chemicals would be highly advantageous.

BRIEF SUMMARY OF THE INVENTION

The invention relates to methods, microorganisms and compositions useful for processing lignocellulosic hydrolysates. The present invention pertains to an isolated *Thermoanaerobacter* sp. cell capable of growing and producing a carbon-based chemical at a temperature of above 70° C. comprising a 16S rDNA sequence of SEQ ID NO 1, and wherein the cell is DIB004G deposited under the DSMZ Accession number 25179.

In a first aspect, embodiments of the invention provide novel isolated saccharolytic and amylolytic or saccharolytic, amylolytic and xylanolytic, respectively, thermophilic bacterial cells belonging to the genus *Thermoanaerobacter*, in particular capable of producing high levels of ethanol and/or lactic acid from lignocellulosic hydrolysates while producing low levels of acetic acid.

Embodiments of this invention relate to an isolated *Thermoanaerobacter* sp. cells comprising a 16S rDNA with a sequence selected form the group consisting of SEQ ID NO. 1, SEQ ID NO. 2, SEQ ID NO. 3, SEQ ID NO. 4, SEQ ID NO. 5, SEQ ID NO. 6, SEQ ID NO. 7 and SEQ ID NO. 8, or homologues thereof.

In one aspect, embodiments of the invention relate to the isolated cells of *Thermoanaerobacter* sp. DIB004G, *Thermoanaerobacter* sp. DIB087G, *Thermoanaerobacter* sp. DIB097X, *Thermoanaerobacter* sp. DIB101G, *Thermoanaerobacter* sp. DIB101X, *Thermoanaerobacter* sp DIB103X, *Thermoanaerobacter* sp. DIB DIB104X or *Thermoanaerobacter* sp. DIB107X, each respectively characterized by having a 16S rDNA sequence at least 99 to 100%, preferably 99.5 to 99.99 percent identical to SEQ ID NO. 1, SEQ ID NO. 2, SEQ ID NO. 3, SEQ ID NO. 4, SEQ ID NO. 5, SEQ ID NO. 6, SEQ ID NO. 7 or SEQ ID NO 8 as outlined in table 1.

In still another aspect the present invention relates to an isolated strain comprising a *Thermoanaerobacter* sp. cell according to any of the preceding aspects.

Accordingly, the invention pertains to isolated *Thermoanaerobacter* sp. strains selected from the group consisting of DIB004G, DIB087G, DIB097X, DIB101G, DIB101X, DIB103X, DIB104X and DIB107X, all listed with their respective accession numbers and deposition dates in table 1, cells derived there from, mutants there from, a progenies or homologues.

In one aspect, the invention is based on the isolation of the *Thermoanaerobacter* strains DIB097X, DIB101X, DIB103X, DIB104X and DIB107X, which are capable of growing and producing high levels of carbon based fermentation products from lignocellulosic hydrolysates and/or directly from poly-, oligo, di- and/or monosaccharides, in particular from poly-, oligo, di- and/or monosaccharides derived from pre-treated lignocellulosic biomass with polysaccharides being limited to hemicelluloses, e.g. xylan and starch.

The invention is further based on the isolation of the *Thermoanaerobacter*sp. strains DIB004G, DIB087G and DIB101G which are capable of growing and producing high levels of carbon based fermentation products from lignocellulosic hydrolysates and/or directly from poly-, oligo, di- and/or monosaccharides, in particular from poly-, oligo, di- and/or monosaccharides derived from pre-treated lignocellulosic biomass with polysaccharides being limited to starch.

One of the advantages of the microorganisms according to the present invention and mutants thereof are the broad substrate specificity, since they are capable of utilizing pentoses such as xylose and arabinose and of hexoses such as glucose, mannose, fructose and galactose. The strains further have the advantage of being extremely thermophilic and thus are capable of growing at very high temperatures resulting in high productivities and substrate conversion rates, low risk of contamination and facilitated product recovery.

In still another aspect, embodiments of the invention relate to an isolated *Thermoanaerobacter* sp. cell comprising a 16S rDNA comprising the sequence SEQ ID NO 1.

In another aspect, embodiments of the invention relate to an isolated *Thermoanaerobacter* sp. DIB004G characterized by having a 16S rDNA sequence at least 99 percent, preferably 99.5 to 99.99 percent identical to SEQ ID NO 1.

In still another aspect, embodiments of the invention relate to an isolated *Thermoanaerobacter* sp. cell comprising a 16S rDNA comprising the sequence SEQ ID NO 2.

In another aspect, embodiments of the invention relate to an isolated *Thermoanaerobacter* sp. DIB087G characterized by having a 16S rDNA sequence at least 99 percent, preferably 99.5 to 99.99 percent identical to SEQ ID NO 2.

In still another aspect, embodiments of the invention relate to an isolated *Thermoanaerobacter* sp. cell comprising a 16S rDNA comprising the sequence SEQ ID NO 3.

In another aspect, embodiments of the invention relate to an isolated *Thermoanaerobacter* sp. DIB097X characterized by having a 16S rDNA sequence at least 99 percent, preferably 99.5 to 99.99 percent identical to SEQ ID NO 3.

In still another aspect, embodiments of the invention relate to an isolated *Thermoanaerobacter* sp. cell comprising a 16S rDNA comprising the sequence SEQ ID NO 4.

In another aspect, embodiments of the invention relate to an isolated *Thermoanaerobacter* sp. DIB101G characterized by having a 16S rDNA sequence at least 99 percent, preferably 99.5 to 99.99 percent identical to SEQ ID NO 4.

In still another aspect, embodiments of the invention relate to an isolated *Thermoanaerobacter* sp. cell comprising a 16S rDNA comprising the sequence SEQ ID NO 5.

In another aspect, embodiments of the invention relate to an isolated *Thermoanaerobacter* sp. DIB101X characterized by having a 16S rDNA sequence at least 99 percent, preferably 99.5 to 99.99 percent identical to SEQ ID NO 5.

In still another aspect, embodiments of the invention relate to an isolated *Thermoanaerobacter* sp. cell comprising a 16S rDNA comprising the sequence SEQ ID NO 6.

In another aspect, embodiments of the invention relate to an isolated *Thermoanaerobacter* sp. DIB103X characterized by having a 16S rDNA sequence at least 99 percent, preferably 99.5 to 99.99 percent identical to SEQ ID NO 6.

In still another aspect, embodiments of the invention relate to an isolated *Thermoanaerobacter* sp. cell comprising a 16S rDNA comprising the sequence SEQ ID NO 7.

In another aspect, embodiments of the invention relate to an isolated *Thermoanaerobacter* sp. DIB104X characterized by having a 16S rDNA sequence at least 99 percent, preferably 99.5 to 99.99 percent identical to SEQ ID NO 7.

In still another aspect, embodiments of the invention relate to an isolated *Thermoanaerobacter* sp. cell comprising a 16S rDNA comprising the sequence SEQ ID NO 8.

In another aspect, embodiments of the invention relate to an isolated *Thermoanaerobacter* sp. DIB107 characterized by having a 16S rDNA sequence at least 99 percent, preferably 99.5 to 99.99 percent identical to SEQ ID NO 8.

In another aspect the present invention relates to an isolated strain comprising a *Thermoanaerobacter* sp. cell according to any of the preceding aspects.

In a further aspect, embodiments of the invention relate to microorganism of the strain *Thermoanaerobacter* sp. DIB004G deposited as DSM 25179, a microorganism derived there from or a *Thermoanaerobacter* sp. DIB004G homolog or mutant.

In a further aspect, embodiments of the invention relate to microorganism of the strain *Thermoanaerobacter* sp.

DIB087G deposited as DSM 25777, a microorganism derived there from or a *Thermoanaerobacter* sp. DIB087G homolog or mutant.

In a further aspect, embodiments of the invention relate to microorganism of the strain *Thermoanaerobacter* sp. DIB097X deposited as DSM 25308, a microorganism derived there from or a *Thermoanaerobacter* sp. DIB097X homolog or mutant.

In a further aspect, embodiments of the invention relate to microorganism of the strain *Thermoanaerobacter* sp. DIB101G deposited as DSM 25180, a microorganism derived there from or a *Thermoanaerobacter* sp. DIB101G homolog or mutant.

In a further aspect, embodiments of the invention relate to microorganism of the strain *Thermoanaerobacter* sp. DIB101X deposited as DSM 25181, a microorganism derived there from or a *Thermoanaerobacter* sp. DIB101X homolog or mutant.

In a further aspect, embodiments of the invention relate to microorganism of the strain *Thermoanaerobacter* sp. DIB103X deposited as DSM 25776, a microorganism derived there from or a *Thermoanaerobacter* sp. DIB103X homolog or mutant.

In a further aspect, embodiments of the invention relate to microorganism of the strain *Thermoanaerobacter* sp. DIB104X deposited as DSM 25778, a microorganism derived there from or a *Thermoanaerobacter* sp. DIB104X homolog or mutant.

In a further aspect, embodiments of the invention relate to microorganism of the strain *Thermoanaerobacter* sp. DIB107X deposited as DSM 25779, a microorganism derived there from or a *Thermoanaerobacter* sp. DIB107X homolog or mutant.

In another aspect the invention relates to methods of producing one or more fermentation products comprising culturing one or more cells or strains according to the disclosure under suitable conditions.

In still another aspect, embodiments of the invention relate to methods for converting lignocellulosic hydrolysates to a biofuel or another carbon-based chemical, comprising the step of contacting the lignocellulosic hydrolysates with a microbial culture for a period of time at an initial temperature and an initial pH, thereby producing an amount of biofuel and/or other carbon-based products; wherein the microbial culture comprises an extremely thermophilic microorganism of the genus *Thermoanaerobacter*, in particular any microorganism of the strain *Thermoanaerobacter* sp. listed in table 1 with their respective accession numbers, microorganisms derived there from, mutants or homologous thereof.

In another aspect, embodiments of the invention relate to methods for converting starch or starch-containing feedstock to a biofuel or another carbon-based chemical, comprising the step of contacting the starch-containing feedstock with a microbial culture for a period of time at an initial temperature and an initial pH, thereby producing an amount of biofuel and/or other carbon-based products; wherein the microbial culture comprises an extremely thermophilic microorganism of the genus *Thermoanaerobacter*, in particular any microorganism of the strain *Thermoanaerobacter* sp. listed in table 1 with their respective accession numbers, microorganisms derived there from, mutants or homologous thereof.

In still another aspect, embodiments of the invention relate to methods for converting a combination or mixture of lignocellulosic hydrolysates and starch-containing feedstock to a biofuel or another carbon-based chemical, comprising the step of contacting the mixture with a microbial culture for a period of time at an initial temperature and an initial pH, thereby producing an amount of biofuel and/or other carbon-based products; wherein the microbial culture comprises an extremely thermophilic microorganism of the genus *Thermoanaerobacter*, in particular any microorganism of the strain *Thermoanaerobacter* sp. listed in table 1 with their respective accession numbers, microorganisms derived there from, mutants or homologous thereof.

Further, embodiments of the invention relate to compositions for converting lignocellulosic hydrolysates or a microbial culture comprising a cell, strain or microorganism according to the present disclosure.

Further, embodiments of the invention relate to the use of a cell, strain, microorganism and/or a microbial culture according to the present disclosure for the production of ethanol and/or lactic acid, a salt or an ester thereof It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 2 shows a 16S rDNA from *Thermoanaerobacter* sp. DIB004G cell.

FIG. 3 shows a 16S rDNA from *Thermoanaerobacter* sp. DIB087G cell.

FIG. 4 shows a 16S rDNA from *Thermoanaerobacter* sp. DIB097X cell.

FIG. 5 shows a 16S rDNA from *Thermoanaerobacter* sp. DIB101G cell.

FIG. 6 shows a 16S rDNA from *Thermoanaerobacter* sp. DIB101X cell.

FIG. 7 shows a 16S rDNA from *Thermoanaerobacter* sp. DIB103X cell.

FIG. 8 shows a 16S rDNA from *Thermoanaerobacter* sp. DIB104X cell.

FIG. 9 shows a 16S rDNA from *Thermoanaerobacter* sp. DIB107X cell.

FIG. 10 shows a table indicating performance data from all strains listed in table 1 during cultivation on cellobiose, glucose, xylane and xylose.

FIG. 11 shows a table indicating performance data from all strains listed in table 1 during cultivation on pretreated poplar wood and performance data from selected strains DIB004G and DIB097X on different lignocellulosic feedstock types.

DETAILED DESCRIPTION

Figure 1:
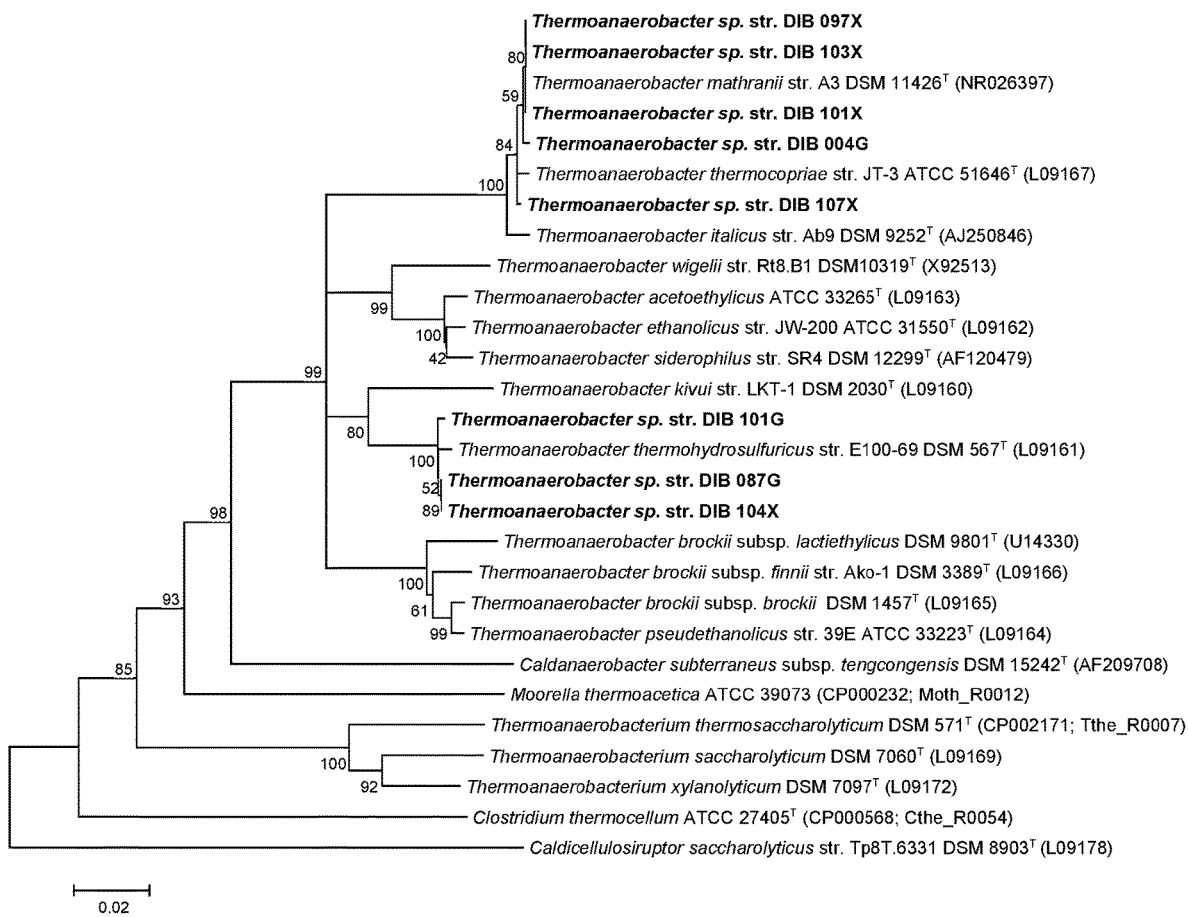
FIG. 1 illustrates a phylogenetic tree based on 16S rDNA genes for all *Thermoanaerobacter* sp. strains comprised in the invention as listed in table 1.

As mentioned above, the invention relates to methods, microorganisms, and compositions useful for processing lignocellulosic hydrolysates. The invention relates, in certain aspects, to microorganisms which are able to convert pretreated lignocellulosic biomass such as, for example, poplar wood chips or *miscanthus* grass, to an economically desirable product such as, for example, a biofuel (e.g., an alcohol and/or hydrogen gas (H2)), polymer, or commodity carbon-based chemical like lactic acid. Furthermore, the invention relates to methods, microorganisms, and compositions useful for converting sugars like poly-, oligo, di- and/or mono-saccharides, in particular poly-, oligo, di- and/or mono-saccharides of hexoses and/or poly-, oligo, di- and/or monosaccharides of pentoses to produce carbon based chemicals like ethanol and/or lactic acid.

The present inventors have found microorganisms of the genus *Thermoanaerobacter* which have a variety of advantageous properties for their use in the conversion of oligosaccharides, disaccharides and/or monosaccharides of hexoses and polysaccharides, oligosaccharides, disaccharides and/or monosaccharides of pentoses, in particular derived from lignocellulosic hydrolysates to high level of ethanol and/or lactic acid while producing low level of acetic acid.

It is an advantage of the microorganisms according to the present disclosure that the microorganisms are able to convert highly complex polysaccharides like xylan to high yields of carbon based chemicals like ethanol and/or lactic acid.

In particular, these microorganisms are extreme thermophiles and show a broad substrate specificities and high natural production of ethanol as well as lactic acid. Moreover, ethanol and lactic acid fermentation at high temperatures, for example over 70° C. has many advantages over mesophilic fermentation. One advantage of thermophilic fermentation is the minimization of the problem of contamination in continuous cultures, since only a few microorganisms are able to grow at such high temperatures in undetoxified lignocellulose hydrolysate.

In the present context the term "lignocellulosic hydrolysate" is intended to designate a lignocellulosic biomass which has been subjected to a pre-treatment step whereby lignocellulosic material has been at least partially separated into cellulose, hemicellulose and lignin thereby having increased the surface area of the material. The lignocellulosic material may typically be derived from plant material, such as straw, hay, garden refuse, comminuted wood, fruit hulls and seed hulls.

The term "a microorganism" as used herein may refer to only one unicellular organism as well as to numerous single unicellular organisms. For example, the term "a microorganism of the genus *Thermoanaerobacter*" may refer to one single *Thermoanaerobacter* bacterial cell of the genus *Thermoanaerobacter* as well as to multiple bacterial cells of the genus *Thermoanaerobacter*.

The terms "a strain of the genus *Thermoanaerobacter*" and "a *Thermoanaerobacter* cell" are used synonymously herein. In general, the term "microorganisms" refers to numerous cells. In particular, said term refers to at least 103 cells, preferably at least 104 cells, at least 105 or at least 106 cells.

A strain "homolog" as used herein is considered any bacterial strain, which is not significantly different by means of DNA homology as defined above and exhibits same or comparable physiological properties as described in the examples herein.

The term "mutant" as used herein refers to a bacterial cell in which the genome, including one or more chromosomes or potential extra-chromosomal DNA, has been altered at one or more positions, or in which DNA has been added or removed.

As used herein "mutant" or "homolog" means also a microorganism derived from the cells or strains according to the present disclosure, which are altered due to a mutation. A mutation is a change produced in cellular DNA, which can be spontaneous, caused by an environmental factor or errors in DNA replication, or induced by physical or chemical conditions. The processes of mutation included in this and indented subclasses are processes directed to production of essentially random changes to the DNA of the microorganism including incorporation of exogenous DNA. All mutants of the microorganisms comprise the advantages of being extreme thermophile (growing and fermenting at temperatures above 70° C.) and are capable of fermenting lignocellulosic biomass to ethanol and/or lactic acid. In an advantageous embodiment, mutants of the microorganisms according to the present disclosure have in a DNA-DNA hybridization assay, a DNA-DNA relatedness of at least 80%, preferably at least 90%, at least 95%, more preferred at least 98%, most preferred at least 99%, and most preferred at least 99.9% with one of the isolated bacterial strains DIB004G, DIB087G, DIB097X, DIB101G, DIB101X, DIB103X, DIB104X and DIB107X.

The term "progeny" is refers to a product of bacterial reproduction, a new organism produced by one or more parents.

As mentioned above lignocellolytic biomass according to the present disclosure can be grass, switch grass, cord grass, rye grass, reed canary grass, mixed prairie grass, *miscanthus*, Napier grass, sugar-methoding residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, pressmud from sugar beet, cotton stalk, banana leaves, oil palm residues and lignocellulosic biomass material obtained through processing of food plants. In advantageous embodiments, the lignocellulosic biomass material is hardwood and/or softwood, preferably poplar wood. In advantageous embodiments, the lignocellulosic biomass material is a grass or perennial grass, preferably *miscanthus*.

The term "DNA-DNA relatedness" in particularly refers to the percentage similarity of the genomic or entire DNA of two microorganisms as measured by the DNA-DNA hybridization/renaturation assay according to De Ley et al. (1970) Eur. J. Biochem. 12, 133-142 or Huß et al. (1983) Syst. Appl. Microbiol. 4, 184-192. In particular, the DNA-DNA hybridization assay preferably is performed by the DSMZ (Deutsche Sammlung von Mikroorganismen and Zellkulturen GmbH, Braunschweig, Germany) Identification Service.

The term "16S rDNA gene sequence similarity" in particular refers to the percentage of identical nucleotides between a region of the nucleic acid sequence of the 16S ribosomal RNA (rDNA) gene of a first microorganism and the corresponding region of the nucleic acid sequence of the 16S rDNA gene of a second microorganism. Preferably, the region comprises at least 100 consecutive nucleotides, more preferably at least 200 consecutive nucleotides, at least 300 consecutive nucleotides or at least 400 consecutive nucleotides, most preferably about 480 consecutive nucleotides.

The strains according to disclosure have the potential to be capable of producing a number of different fermentation products, including acids, alcohols, ketones and hydrogen. In one embodiment, the alcohol is selected from ethanol, butanol, propanol, methanol, propanediol and butanediol. In a further embodiment the acid is lactic acid, propionic acid, acetic acid, succinic acid, butyric acid or formic acid and the ketone is acetone.

In advantageous embodiments, the lignocellulosic biomass material is subjected to mechanical, thermochemical, and/or biochemical pretreatment. The lignocellulosic biomass material could be exposed to steam treatment. In further embodiments, the lignocellulosic biomass material is pretreated with mechanical comminution and a subsequent treatment with lactic acid, acetic acid, sulfuric acid or sulfurous acid or their respective salts or anhydrides under heat and pressure with or without a sudden release of pressure. In another embodiment, the lignocellulosic biomass material is pretreated with mechanical comminution and a subsequent treatment with either sodium hydroxide, ammonium hydroxide, calcium hydroxide or potassium hydroxide under heat and pressure with or without a sudden release of pressure.

In advantageous embodiments, the lignocellulosic biomass material is pretreated with mechanical comminution and subsequent exposure to a multi-step combined pretreatment process. Such multi-step combined pretreatment may include a treatment step consisting of cooking in water or steaming of the lignocellulosic biomass material at a temperature of 100-200° C. for a period of time in between 5 and 120 min. Suitable catalysts include lactic acid, acetic acid, sulfuric acid, sulfurous acid, sodium hydroxide, ammonium hydroxide, calcium hydroxide or potassium hydroxide or their respective salts or anhydrides may or may not be added to the process. The process may further include a step comprising a liquid-solid separation operation, e.g. filtration, separation, centrifugation or a combination thereof, separating the process fluid containing partially or fully hydrolyzed and solubilized constituents of the lignocellulosic biomass material from the remaining insoluble parts of the lignocellulosic biomass. The process may further include a step comprising washing of the remaining lignocellulosic biomass material. The solid material separated from solubilized biomass constituents may then be treated in a second step with steam under heat and pressure with or without a sudden release of pressure at a temperature of 150-250° C. for a period of time in between 1 and 15 min. In order to increase pretreatement effectiveness, a suitable catalyst includes lactic acid, acetic acid, sulfuric acid, sulfurous acid, sodium hydroxide, ammonium hydroxide, calcium hydroxide or potassium hydroxide or their respective salts or anhydrides may be added also to the second step.

In advantageous embodiments, the lignocellulosic biomass is milled before converted into biofuels like ethanol and/or carbon-based chemicals like lactic acid. In one embodiment, the lignocellulosic biomass is pretreated biomass from *Populus* sp, preferably pretreated with steam pretreatment or multi-step combined pretreatment. In another embodiment, the lignocellulosic biomass is pretreated biomass from any perennial grass, e.g. *Miscanthus* sp., preferably treated with steam pretreatment or multi-step combined pretreatment.

In further advantageous embodiments the lignocellulosic hydrolysate is then treated with an enzymatic hydrolysis with one or more appropriate carbohydrase enzymes such as cellulases, glucosidases and/or hemicellulases including xylanases.

The pretreatment method most often used is steam pretreatment, a process comprising heating of the lignocellulosic material by steam injection to a temperature of 130-230 degrees centigrade with or without subsequent sudden release of pressure. Prior to or during steam pretreatment, a catalyst like a mineral or organic acid or a caustic agent facilitating disintegration of the biomass structure can be added optionally. Catalysts often used for such a pretreatment include sulphuric acid, sulphurous acid, hydrochloric acid, acetic acid, lactic acid, sodium hydroxide (caustic soda), potassium hydroxide, calcium hydroxide (lime), ammonia or the respective salts or anhydrides of any of these agents.

Such steam pretreatment step may or may not be preceded by another treatment step including cooking of the biomass in water or steaming of the biomass at temperatures of 100-200° C. with or without the addition of a suitable catalyst like a mineral or organic acid or a caustic agent facilitating disintegration of the biomass structure. In between the cooking step and the subsequent steam pretreatment step one or more liquid-solid-separation and washing steps can be introduced to remove solubilized biomass components in order to reduce or prevent formation of inhibitors during the subsequent steam pretreatment step. Inhibitors formed during heat or steam pretreatment include furfural formed from monomeric pentose sugars, hydroxymethylfurfural formed from monomeric hexose sugars, acetic acid, levulinic acid, phenols and phenol derivatives.

Another type of lignocellulose hydrolysis is acid hydrolysis, where the lignocellulosic material is subjected to an acid such as sulfuric acid or sulfurous acid whereby the sugar polymers cellulose and hemicellulose are partly or completely hydrolysed to their constituent sugar monomers. A third method is wet oxidation wherein the material is treated with oxygen at 150-185 degrees centigrade. The pretreatments can be followed by enzymatic hydrolysis to complete the release of sugar monomers. This pre-treatment step results in the hydrolysis of cellulose into glucose while hemicellulose is transformed into the pentoses xylose and arabinose and the hexoses glucose, mannose and galactose. The pretreatment step may in certain embodiments be supplemented with treatment resulting in further hydrolysis of the cellulose and hemicellulose. The purpose of such an additional hydrolysis treatment is to hydrolyze oligosaccharide and possibly polysaccharide species produced during the acid hydrolysis, wet oxidation, or steam pretreatment of cellulose and/or hemicellulose origin to form fermentable sugars (e.g. glucose, xylose and possibly other monosaccharides). Such further treatments may be either chemical or enzymatic. Chemical hydrolysis is typically achieved by treatment with an acid, such as treatment with aqueous sulphuric acid or hydrochloric acid, at a temperature in the range of about 100-150 degrees centigrade. Enzymatic hydrolysis is typically performed by treatment with one or more appropriate carbohydrase enzymes such as cellulases, glucosidases and hemicellulases including xylanases.

It has been found that the microorganisms according to the present disclosure can grow efficiently on various types of pretreated and untreated biomass (e.g. wood incl. poplar, spruce and cotton wood; various types of grasses and grass residues incl. *miscanthus*, wheat straw, sugarcane bagasse, corn stalks, corn cobs, whole corn plants, sweet sorghum).

As used herein "efficient" growth refers to growth in which cells may be cultivated to a specified density within a specified time.

The microorganisms according to the present disclosure can grow efficiently on hydrolysis products of cellulose (e.g. disaccharide cellobiose), cellulose derived hexoses (e.g. glucose), unhydrolyzed hemicelluloses like xylan, hemicellulose derived pentoses (e.g. xylose), unhydrolyzed amyloseas well as steam pretreated poplar or *miscanthus*. In particular, the main products when grown on cellobiose, glucose and xylose may be ethanol and lactic acids. The main product when grown on pretreated biomass substrates was ethanol, for example, when the microorganisms were grown on steam-pretreated poplar wood or *miscanthus* grass the ethanol yield is high. The microorganisms according to the present disclosure also grow efficiently on cellobiose.

Cellobiose is a disaccharide derived from the condensation of two glucose molecules linked in a β(1→4) bond. It can be hydrolyzed to give glucose. Cellobiose has eight free alcohol (OH) groups, one either linkage or two hemiacetal linkages, which give rise to strong inter- and intra-molecular hydrogen bonds. It is a type of dietary carbohydrate also found in mushrooms.

Xylan is a generic term used to describe a wide variety of highly complex polysaccharides that are found in plant cell walls and some algae. Xylans are polysaccharides made from units of xylose.

Furthermore, the microorganisms according to the present disclosure grew efficiently on the soluble materials obtained after heat treating of lignocellulosic biomass.

It was surprisingly found that the bacterial subspecies according to the present disclosure is capable of growing in a medium comprising a lignocellulosic hydrolysates having a dry-matter content of at least 10 percent wt/wt, such as at least 15 percent wt/wt, including at least 20 percent wt/wt, and even as high as at least 25 percent wt/wt.

The microorganisms according to the invention are anaerobic thermophile bacteria, and they are capable of growing at high temperatures even at or above 70 degrees centigrade. The fact that the strains are capable of operating at this high temperature is of high importance in the conversion of the lignocellulosic hydrolysates into fermentation products. The conversion rate of carbohydrates into e.g. ethanol and/or lactic is much faster when conducted at high temperatures. For example, the volumetric ethanol productivity of a thermophilic *Bacillus* is up to ten-fold higher than a conventional yeast fermentation process which operates at 30 degrees centigrade. Consequently, a smaller production plant is required for a given plant capacity, thereby reducing plant construction costs. As also mentioned previously, the high temperature reduces the risk of contamination from other microorganisms, resulting in less downtime, increased plant productivity and a lower energy requirement for feedstock sterilization. The high operation temperature may also facilitate the subsequent recovery of the resulting fermentation products.

Lignocellulosic biomass material and lignocellulose hydrolysates contain inhibitors such as furfural, phenols and carboxylic acids, which can potentially inhibit the fermenting organism. Therefore, it is an advantage of the microorganisms according to the present disclosure that they are tolerant to these inhibitors.

The microorganisms according to the present disclosure are novel species of the genus *Thermoanaerobacter* or novel subspecies of *Thermoanaerobacter mathranii*.

For example, the genus *Thermoanaerobacter* includes different species of extremely thermophilic (temperature optima for growth higher than 70° C.) hemicellulolytic and saccharolytic strictly anaerobic bacteria (Lee et al. 1993). *Thermoanaerobacter mathranii* DSM 11426 is an extremely thermophilic bacterium. It has a temperature optimum between 70 and 75° C. and was isolated from a hot spring in Iceland (Larsen et al. 1997). It uses a number of sugars including xylan as carbon sources, but did not utilize microcrystalline cellulose. Fermentation end products on xylose were ethanol, acetate, low amounts of lactate, $CO_2$, and $H_2$ (Larsen et al. 1997).

According to the present disclosure, the microorganisms produce ethanol and lactic acid and show several features that distinguish them from currently used microorganisms: (i) high yield and low product inhibition, (ii) simultaneous utilization of lignocellolosic biomass material derived sugars, and (iii) growth at elevated temperatures. The microorganisms according to the present disclosure are robust thermophilic organisms with a decreased risk of contamination. They efficiently convert an extraordinarily wide range of biomass components to carbon-based chemicals like ethanol or lactic acid.

As mentioned above, in one aspect, the present disclosure relates to an isolated cell comprising a 16S rDNA sequence selected from the group consisting of: SEQ ID NO 1, SEQ ID NO 2, SEQ ID NO 3, SEQ ID NO 4, SEQ ID NO 5, SEQ ID NO 6, SEQ ID NO 7, SEQ ID NO 8 and a combination of any thereof.

In one aspect, the present disclosure pertains to an isolated *Thermoanaerobacter* sp. cell having a 16S rDNA sequence at least 99, at least 99.3, at least 99.5, at least, 99.7, at least 99.9, at least 99.99 percent identical to SEQ ID NO 1, SEQ ID NO 2, SEQ ID NO 3, SEQ ID NO 4, SEQ ID NO 5, SEQ ID NO 6, SEQ ID NO 7 and/or SEQ ID NO 8.

In one embodiment of the present disclosure the isolated cell is *Thermoanaerobacter* sp. DIB004G (DSMZ Accession number 25179), cells derived there from, mutants there from, a progeny or a *Thermoanaerobacter* sp. DIB004G homolog or mutant.

In another embodiment of the present disclosure the isolated cell is *Thermoanaerobacter* sp. DIB087G (DSMZ Accession number 25777), cells derived there from, mutants there from, a progeny or a *Thermoanaerobacter* sp. DIB087G homolog or mutant.

In another embodiment of the present disclosure the isolated cell is *Thermoanaerobacter* sp. DIB097X (DSMZ Accession number 25308), cells derived there from, mutants there from, a progeny or a *Thermoanaerobacter* sp. DIB097X homolog or mutant.

In another embodiment of the present disclosure the isolated cell is *Thermoanaerobacter* sp. DIB101G (DSMZ Accession number 25180), cells derived there from, mutants there from, a progeny or a *Thermoanaerobacter* sp. DIB101G homolog or mutant.

In another embodiment of the present disclosure the isolated cell is *Thermoanaerobacter* sp. DIB101X (DSMZ Accession number 25181), cells derived there from, mutants there from, a progeny or a *Thermoanaerobacter* sp. DIB101X homolog or mutant.

In another embodiment the isolated cell is *Thermoanaerobacter* sp. DIB103X (DSMZ Accession number 25776), cells derived there from, mutants there from, a progeny or a *Thermoanaerobacter* sp. DIB103X homolog or mutant.

In another embodiment the isolated cell is *Thermoanaerobacter* sp. DIB104X (DSMZ Accession number 25778), cells derived there from, mutants there from, a progeny or a *Thermoanaerobacter* sp. DIB104X homolog or mutant.

In another embodiment the isolated cell is *Thermoanaerobacter* sp. DIB107X (DSMZ Accession number 25779), cells derived there from, mutants there from, a progeny or a *Thermoanaerobacter* sp. DIB107X homolog or mutant.

The invention is based on the isolated bacterial strains *Thermoanaerobacter* sp. as listed in table 1 that contain 16S rDNA sequences 100 percent and/or 99.99 percent identical to the respectively list sequences.

TABLE 1

| Genus | Species | Name | DSMZ accession number | Deposition date | 16SrDNA SEQ ID NO. |
|---|---|---|---|---|---|
| Thermoanaerobacter | sp. | DIB004G | DSM 25179 | 15.09.2011 | 1 |
| Thermoanaerobacter | sp. | DIB087G | DSM 25777 | 15.03.2012 | 2 |
| Thermoanaerobacter | sp. | DIB097X | DSM 25308 | 27.10.2011 | 3 |
| Thermoanaerobacter | sp. | DIB101G | DIB 25180 | 15.09.2011 | 4 |
| Thermoanaerobacter | sp. | DIB101X | DSM 25181 | 15.09.2011 | 5 |
| Thermoanaerobacter | sp. | DIB103X | DSM 25776 | 15.03.2012 | 6 |
| Thermoanaerobacter | sp. | DIB104X | DSM 25778 | 15.03.2012 | 7 |
| Thermoanaerobacter | sp. | DIB107X | DSM 25779 | 15.03.2012 | 8 |

All strains as listed in table 1 have been deposited in accordance with the terms of the Budapest Treaty on Sep. 15, 2011 with DSMZ—Deutsche Sammlung von Mikroorganismen and Zellkulturen GmbH, Inhoffenstr. 7B, 38124 Braunschweig, Germany—under the respectively indicated accession numbers and deposition dates by DIREVO Industrial Biotechnology GmbH, Nattermannallee 1, 50829 Cologne, Germany (DE).

As is apparent from the following, the preferred strains of the present disclosure have been deposited. Other cells, strains, bacteria, microorganisms and/or microbial cultures of the present disclosure can therefore be obtained by mutating the deposited strains and selecting derived mutants having enhanced characteristics. Desirable characteristics include an increased range of sugars that can be utilized, increased growth rate, ability to produce higher amounts of fermentation products such as ethanol and/or lactic acid, etc. Suitable methods for mutating bacteria strains and selecting desired mutants are described in Functional analysis of Bacterial genes: A practical Manual, edited by W. Schumann, S. D. Ehrlich & N. Ogasawara, 2001.

The microorganisms of the species *Thermoanaerobacter* sp. according to the present disclosure in particular refer to a microorganism which belongs to the genus *Thermoanaerobacter* and which preferably has one or more of the following characteristics:
a) it is a microorganism of the genus *Thermoanaerobacter*; and/or
b) in a DNA-DNA hybridization assay, it shows a DNA-DNA relatedness of at least 70%, preferably at least 90%, at least 95%, more preferred at least 98%, most preferred at least 99% with the *Thermoanaerobacter* sp. strains listed in table 1 with their respective accession numbers; and/or
c) it displays a level of 16S rDNA gene sequence similarity of at least 98%, preferably at least 99% or at least 99.5%, more preferably 100% with either of the *Thermoanaerobacter* sp. strains listed in table 1 with their respective accession numbers; and/or
d) it is capable of surviving and/or growing and/or producing high levels of at least one fermentation product at high temperature conditions above 70° C., and/or
e) it is a Gram-positive bacterium; and/or
f) it is saccharolytic thermophilic microorganism; and/or
g) it is a xylanolytic thermophilic microorganism.

Preferably, at least two or at least three, and more preferred all of the above defined criteria a) to g) are fulfilled.

In an advantageous embodiment, the microorganisms according to the present disclosure in particular refer to a microorganism which belongs to the genus *Thermoanaerobacter* and which preferably has one or more of the following characteristics:

a) It is a microorganism of the genus *Thermoanaerobacter*;
b) it is a microorganism of the species *Thermoanaerobacter thermohydrosulfuricus*, *Thermoanaerobacter thermocopriae* or *Thermoanaerobacter mathranii*;
c) in a DNA-DNA hybridization assay, it shows a DNA-DNA relatedness of at least 80%, preferably at least 90%, at least 95%, more preferred at least 98%, most preferred at least 99%, and most preferred at least 99.9% with one of the strains of table 1; and/or
d) it displays a level of 16S rDNA gene sequence similarity of at least 98%, preferably at least 99%, at least 99.5% or at least 99.7%, more preferably 99.99% with one of the strains listed in table 1; and/or
e) it is capable of surviving and/or growing and/or producing a fermentation product selected from the group consisting of carboxylic acids, preferably lactic acid and alcohols, preferably ethanol at temperature conditions above 70° C., in particular of above 72° C.

Preferably, at least two or at least three, and more preferred all of the above defined criteria a) to e) are fulfilled.

The *Thermoanaerobacter* sp. strains according to the present disclosure have several highly advantageous characteristics needed for the conversion of lignocellulosic biomass material. Thus, these base strains possess all the genetic machinery for the conversion of both pentose and hexose sugars to various fermentation products such as ethanol and lactic acid. As will be apparent from the below examples, the examination of the complete 16S rDNA sequence showed that the related strains *Thermoanaerobacter* sp. DIB087G, *Thermoanaerobacter* sp. DIB101G and *Thermoanaerobacter* sp. DIB104X may be related to *Thermoanaerobacter thermohydrosulfuricus*, although the 16S rDNA sequences clearly place them in separate subspecies or even different species. The strain *Thermoanaerobacter* sp. DIB107X may be related to *Thermoanaerobacter thermocopriae*, although the 16S rDNA sequences clearly place them in separate subspecies or even different species. The strains *Thermoanaerobacter* sp. DIB004G, *Thermoanaerobacter* sp. DIB097X, *Thermoanaerobacter* sp. DIB101X and *Thermoanaerobacter*sp. DIB103X may be related to *Thermoanaerobacter mathranii*, although the 16S rDNA sequences clearly place them in separate subspecies or even different species.

It is a great advantage of the *Thermoanaerobacter* sp. strains according to the present disclosure that they are xylanolytic and saccharolytic (ferment hemicelluloses, e.g. xylan, hexoses and pentoses to ethanol, lactate and small amounts of acetate).

In a preferred embodiment, the *Thermoanaerobacter* sp. microorganism is
a) Either *Thermoanaerobacter* sp. listed in table 1, deposited under their respectively indicated accession number and deposition date, according to the requirements of the Budapest Treaty at the Deutsche Sammlung von Mikroorganismen and Zellkulturen (DSMZ), Inhoffenstraße 7B, 38124 Braunschweig (DE) by DIREVO Industrial Biotechnology GmbH, Nattermannallee 1, 50829 Cologne, Germany (DE), or b) a microorganism derived from either of these *Thermoanaerobacter* sp. strains, or c) a homolog or mutant of either respective *Thermoanaerobacter* sp. Strain.

All strains *Thermoanaerobacter* sp. as listed in table 1 belong to the genus *Thermoanaerobacter* and are extremely thermophilic (growth at temperatures higher than 70° C.), xylanolytic, amylolytic and saccharolytic, strictly anaerobic, Gram-positive bacteria. Cells are straight rods 0.3-0.4 µm by 2.0-6.0 µm, occurring both singly and in pairs. These strains grow on various sugars as substrate, including starch, xylan, xylose, cellobiose, and glucose. The main fermentation products on these substrates are ethanol and lactate. Low amounts of acetate are also formed.

In advantageous embodiments the cells, strains, microorganisms may be modified in order to obtain mutants or derivatives with improved characteristics. Thus, in one embodiment there is provided a bacterial strain according to the disclosure, wherein one or more genes have been inserted, deleted or substantially inactivated. The variant or mutant is typically capable of growing in a medium comprising a lignocellulosic biomass material and/or a lignocellulosic hydrolysate.

In another embodiment, there is provided a process for preparing variants or mutants of the microorganisms according to the present disclosure, wherein one or more genes are inserted, deleted or substantially inactivated as described herein.

In some embodiments one or more additional genes are inserting into the strains according to the present disclosure. Thus, in order to improve the yield of the specific fermentation product, it may be beneficial to insert one or more genes encoding a polysaccharase into the strain according to the invention. Hence, in specific embodiments there is provided a strain and a process according to the invention wherein one or more genes encoding a polysaccharase which is selected from cellulases (such as EC 3.2.1.4); beta-glucanases, including glucan-1,3 beta-glucosidases (exo-1,3 beta-glucanases, such as EC 3.2.1.58), 1,4-beta-cellobiohydrolases (such as EC 3.2.1.91) and endo-1,3(4)-beta-glucanases (such as EC 3.2.1.6); xylanases, including endo-1,4-beta-xylanases (such as EC 3.2.1.8) and xylan 1,4-beta-xylosidases (such as EC 3.2.1.37); pectinases (such as EC 3.2.1.15); alpha-glucuronidases, alpha-L-arabinofuranosidases (such as EC 3.2.1.55), acetylesterases (such as EC 3.1.1.-), acetylxylanesterases (such as EC 3.1.1.72), alpha-amylases (such as EC 3.2.1.1), beta-amylases (such as EC 3.2.1.2), glucoamylases (such as EC 3.2.1.3), pullulanases (such as EC 3.2.1.41), beta-glucanases (such as EC 3.2.1.73), hemicellulases, arabinosidases, mannanases including mannan endo-1,4-beta-mannosidases (such as EC 3.2.1.78) and mannan endo-1,6-alpha-mannosidases (such as EC 3.2.1.101), pectin hydrolases, polygalacturonases (such as EC 3.2.1.15), exopolygalacturonases (such as EC 3.2.1.67) and pectate lyases (such as EC 4.2.2.10), are inserted.

In accordance with the present disclosure, a method of producing a fermentation product comprising culturing a strain according to the invention under suitable conditions is also provided.

The strains according to the disclosure are strictly anaerobic microorganisms, and hence it is preferred that the fermentation product is produced by a fermentation process performed under strictly anaerobic conditions. Additionally, the strain according to invention is an extremely thermophillic microorganism, and therefore the process may perform optimally, when it is operated at temperature in the range of about 40-95 degrees centigrade, such as the range of about 50-90 degrees centigrade, including the range of about 60-85 degrees centigrade, such as the range of about 65-75 degrees centigrade.

For the production of certain fermentation products, it may be useful to select a specific fermentation process, such as batch fermentation process, including a fed-batch process or a continuous fermentation process. Also, it may be useful to select a fermentation reactor such as an immobilized cell reactor, a fluidized bed reactor or a membrane bioreactor.

In accordance with the invention, the method is useful for the production of a wide range of fermentation products including acids, alcohols, ketones and hydrogen. Thus fermentation products such as ethanol, butanol, propanol, methanol, propanediol, butanediol, lactic acid, propionic acid, acetic acid, succinic acid, butyric acid, formic acid and acetone may be produced in accordance with the disclosure.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

The following methods and examples are offered for illustrative purposes only, and are not intended to limit the scope of the present disclosure in any way.

METHODS AND EXAMPLES

In the following examples, materials and methods of the present disclosure are provided including the determination of properties of the strains according to the present disclosure. It should be understood that these examples are for illustrative purpose only and are not to be construed as limiting the invention in any manner.

Example 1: Isolation and Cultivation

All procedures for enrichment and isolation of strains listed in table 1 employed anaerobic technique for strictly anaerobic bacteria (Hungate 1969). The strains were enriched from environmental samples at temperatures higher than 70° C. with crystalline cellulose and beech wood as substrate. Isolation was performed by serial dilutions in liquid media with xylan as substrate followed by picking colonies grown on solid agar medium at 72° C. in Hungate roll tubes (Hungate 1969).

The cells are cultured under strictly anaerobic conditions applying the following medium:

| Basic medium | | |
|---|---|---|
| NH4Cl | 1.0 | g |
| NaCl | 0.5 | g |
| MgSO4 x 7 H2O | 0.3 | g |
| CaCl2 x 2 H2O | 0.05 | g |
| NaHCO3 | 0.5 | g |
| K2HPO4 | 1.5 | g |
| KH2PO4 | 3.0 | g |
| Yeast extract (bacto, BD) | 0.5 | g |
| Cellobiose | 5.0 | g |
| Vitamins (see below) | 1.0 | ml |
| Trace elements (see below) | 0.5 | ml |
| Resazurin | 1.0 | mg |
| Na2S x 9 H2O | 0.75 | g |
| Distilled water | 1000.0 | ml |
| Trace elements stock solution | | |
| $NiCl_2 x 6H_2O$ | 2 | g |
| $FeSO_4 x 7H_2O$ | 1 | g |
| NH4Fe(III) citrate, brown, 21.5% Fe | 10 | g |
| $MnSO_4 x H_2O$ | 5 | g |
| $CoCl_2 x 6H_2O$ | 1 | g |
| $ZnSO_4 x 7H_2O$ | 1 | g |
| $CuSO_4 x 5H_2O$ | 0.1 | g |
| $H_3BO_3$ | 0.1 | g |
| $Na_2MoO_4 x 2H_2O$ | 0.1 | g |
| $Na_2SeO_3 x 5H_2O$ | 0.2 | g |
| $Na_2WoO_4 x 2H_2O$ | 0.1 | g |
| Distilled water | 1000.0 | ml |
| Add 0.5 ml of the trace elements stock solution to 1 liter of the medium | | |
| Vitamine stock solution | | |
| nicotinic acid | 200 | mg |
| cyanocobalamin | 25 | mg |
| p-aminobenzoic acid (4-aminobenzoic acid) | 25 | mg |
| calcium D-pantothenate | 25 | mg |
| thiamine-HCl | 25 | mg |
| riboflavin | 25 | mg |
| lipoic acid | 25 | mg |
| folic acid | 10 | mg |
| biotin | 10 | mg |
| pyridoxin-HCl | 10 | mg |
| Distilled water | 200.0 | ml |

Add 1 ml of the vitamine stock solution to 1 liter of the medium

All ingredients except sulfide are dissolved in deionized water and the medium is flushed with nitrogen gas (purity 99.999%) for 20 min at room temperature. After addition of sulfide, the pH-value is adjusted to 7.0 at room temperature with 1 M HCl. The medium is then dispensed into Hungate tubes or serum flasks under nitrogen atmosphere and the vessels are tightly sealed. After autoclaving at 121° C. for 20 min pH-value should be in between 6.8 and 7.0.

Soluble sugar substrates (xylose, cellobiose, glucose) as specified for individual experiments are added sterile filtered after autoclaving. Xylan is autoclaved with the medium. Subsequent to autoclaving, cultures are inoculated by injection of a seed culture through the seal septum and inoculated in an incubator at 72° C. for the time indicated.

Example 2: HPLC

Sugars and fermentation products were quantified by HPLC-RI using a Via Hitachi LaChrom Elite (Hitachi corp.) fitted with a Rezex ROA Organic Acid H+(Phenomenex). The analytes were separated isocratically with 2.5 mM $H_2SO_4$ and at 65° C.

Example 3: Phylogenetic Analysis of 16S rDNA Genes

Genomic DNA was isolated from cultures grown as described above and 16SrDNA amplified by PCR using 27F (AGAGTTTGATCMTGGCTCAG) as forward and 1492R (GGTTACCTTGTTACGACTT) as reverse primer. The resulting products were sequenced and the sequences analyzed using the Sequencher 4.10.1 software (Gene Codes Corporation). The NCBI database was used for BLAST procedures.

Alignment was carried out using ClustalW (Chenna et al. 2003) and the phylogenetic tree was constructed using software MEGA4 (Kumar et al. 2001). The tree for all strains listed in table 1 is displayed in FIG. 1.

Example 4: Production of Ethanol and Lactate on Different Substrates

Experiments on growth and fermentation on cellobiose, glucose, xylan and xylose as well as on pretreated poplar wood, miscanthus grass, sugarcane bagasse, wheat straw, corn stalks and DDGS as well as on non-pretreated waste paper were performed by cultivation in sealed 16 ml tubes with 8 ml medium described in Example 1. All strains grew well on these substrates (FIGS. 10 and 11) except strains DIB004G, DIB087G and DIB101G which did not grow on xylane. No growth was detected on cellulose. The main fermentation product was ethanol followed by lactate. Only small amounts of acetate were formed (FIGS. 10 and 11). In contrast, the known ethanol-producing thermophilic bacterium Thermoanaerobacter mathranii strain A3 (DSM 11426) (Larsen et al 1997) produced lower amounts of ethanol as well as higher amounts of lactate and acetate.

Example 5: Fermentation

Batch experiments with all strains, e.g. DIB004G, were performed by cultivation on the medium described above with addition of the respectively indicated substrate, e.g. 20 g/L miscanthus grass pretreated with a suitable method selected from those described above comprising heating in the presence of dilute acid followed by sudden release of pressure.

Temperature is controlled to 72° C. and the pH-value is controlled to 6.75±0.1 throughout the fermentation. The fermenter is purged with nitrogen to remove excess oxygen before sodium sulphide is added as described above.

The fermentation is started by addition of a seed culture prepared as described in example 1.

The results of the HPLC analysis as described in example 2 show parallel production of ethanol, lactic acid and acetic acid.

Figure 12:
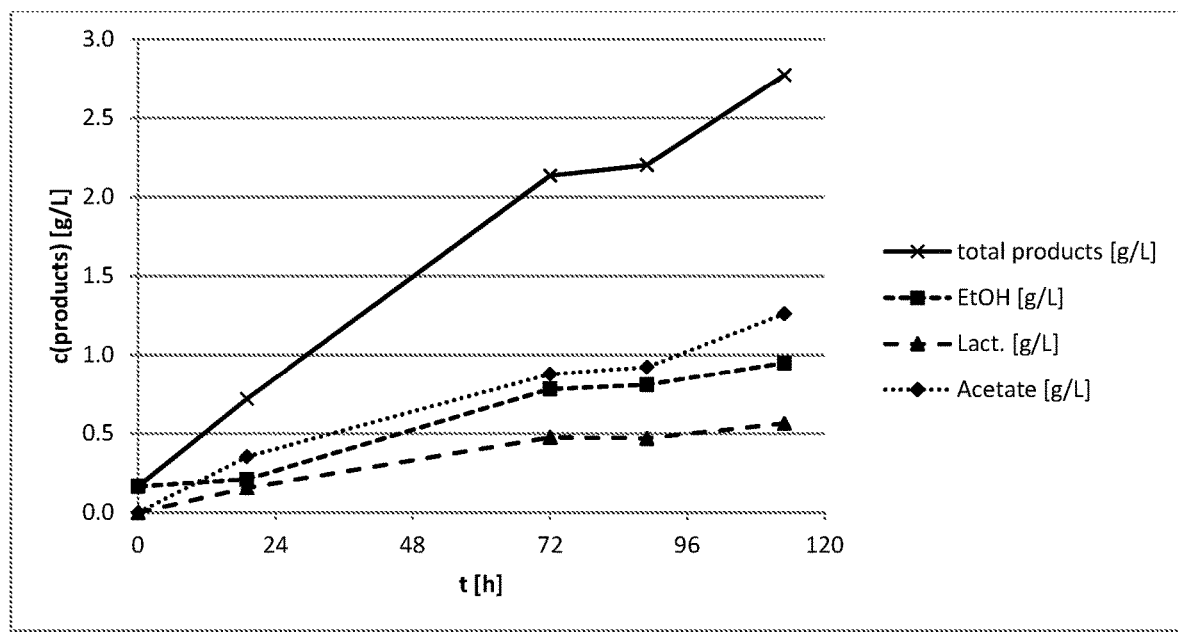
FIG. 12 shows a graph displaying formation of ethanol, lactate and acetate during growth of *Thermoanerobacter* sp. DIB097X on pretreated *miscanthus* grass.
Figure 13:
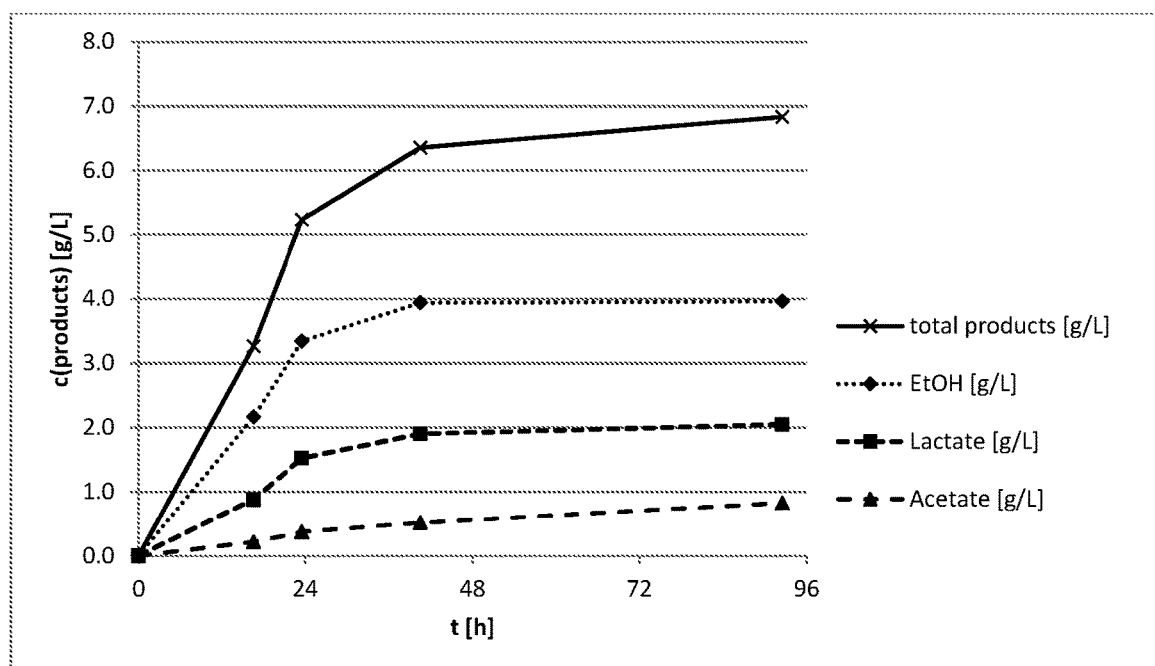
FIG. 13 shows a graph displaying formation of ethanol, lactate and acetate during growth of *Thermoanaerobacter* sp. DIB004G on ground corn seed.

The results for product formation during a fermentation of Thermoanaerobacter sp. DIB097X on pretreated miscanthus grass is shown in FIG. 12. The results for product formation during a fermentation of Thermoanaerobacter sp. DIB004G on non-pretreated ground corn seed is shown in FIG. 13.

Example 6: Production of Lactic Acid by Thermoanaerobacter Strains

Cultivation was performed at 70° C. in sealed 110 ml flasks containing 60 g/l substrate and 50 g/l CaCO3 for pH stabilization.
Cellulose Avicel, starch, xylan, cellobiose, sucrose, lactose, glucose and xylose were applied as substrates.
The main fermentation product with DIB 087G on starch, cellobiose, lactose, glucose and xylose was lactic acid.
The main fermentation product with DIB 104X on starch, cellobiose, lactose, glucose and xylose was lactic acid.
The main fermentation product with DIB 104X on starch, cellobiose, sucrose, glucose and xylose was lactic acid.
The portion of lactic acid (weight-%) in the total fermentation products (lactic acid+acetic acid+ethanol) was generally high and reached 87 weight-% with DIB104X grown on xylose
The portion of L-lactic acid in D,L-lactic produced was 93-99% depending on culture and substrate.

TABLE 2

| Culture | Substrate | Lactic acid g/l | Acetic acid g/l | Ethanol g/l | Lactic acid weight-% | L-lactic acid % from D,L-lactic acid |
|---|---|---|---|---|---|---|
| *Thermoanaerobacter* DIB087 G | Avicel | 0.1 | 0.3 | 0.1 | 19.5 | |
| | Starch | 2.5 | 2.4 | 0.8 | 43.7 | 95.2 |
| | Xylan | 0.3 | 0.3 | 1.0 | 17.2 | |
| | Cellobiose | 5.3 | 1.2 | 0.5 | 75.4 | 98.7 |
| | Sucrose | 0.1 | 0.4 | 0.1 | 23.2 | |
| | Lactose | 3.7 | 1.4 | 0.5 | 66.4 | 97.4 |
| | Glucose | 8.5 | 2.7 | 0.3 | 73.7 | 94.0 |
| | Xylose | 0.9 | 0.4 | 0.0 | 68.2 | |
| | No substrate | 0.1 | 0.2 | 0.1 | 23.0 | |
| *Thermoanaerobacter* DIB104 X | Avicel | 0.1 | 0.2 | 0.2 | 26.6 | |
| | Starch | 6.7 | 1.5 | 3.8 | 55.6 | 95.7 |
| | Xylan | 0.1 | 0.1 | 1.1 | 9.6 | |
| | Cellobiose | 7.7 | 0.8 | 1.6 | 76.0 | 97.9 |
| | Sucrose | 0.2 | 0.3 | 0.3 | 22.0 | |
| | Lactose | 4.6 | 1.1 | 3.0 | 53.0 | 94.8 |
| | Glucose | 7.7 | 2.0 | 1.8 | 66.8 | 92.5 |
| | Xylose | 2.7 | 0.3 | 0.1 | 86.8 | |
| | No substrate | 0.1 | 0.1 | 0.1 | 29.5 | |
| *Thermoanaerobacter* DIB101 X | Avicel | 0.1 | 0.2 | 0.4 | 11.4 | |
| | Starch | 7.4 | 1.6 | 3.5 | 59.2 | 93.7 |
| | Xylan | 0.3 | 0.7 | 7.7 | 3.7 | 78.1 |
| | Cellobiose | 2.9 | 0.9 | 1.9 | 51.7 | 97.6 |
| | Sucrose | 3.8 | 0.8 | 2.3 | 54.9 | 93.2 |
| | Lactose | 1.5 | 1.4 | 2.7 | 27.3 | 94.8 |
| | Glucose | 2.9 | 1.1 | 2.2 | 46.9 | 94.7 |
| | Xylose | 1.2 | 0.2 | 0.0 | 83.5 | |
| | No substrate | 0.0 | 0.1 | 0.2 | 14.3 | |

LIST OF ADDITIONAL REFERENCES

Lee Y-E, Jain M K, Lee c. Lowe S E, Zeikus J G (1993) Taxonomic distinction of saccharolytic thermophilic anaerobes: Description of *Thermoanaerobacterium xylanolyticum* gen. nov., sp. nov., and *Thermoanaerobacterium saccharolyticum* gen. nov., sp. nov.; Reclassification of *Thermoanaerobium brockii*, *Clostridium thermosulfurogenes*, and *Clostridium thermohydrosulfiricum* E100-69 as *Thermoanaerobacter brockii* comb. nov., *Thermoanaerobacterium thermosulfurigenes* comb. nov., and *Thermoanaerobacter thermohydrosulfuricus* comb. nov., respectively; and transfer of *Clostridium hermohydrosulfuricum* 39E to *Thermoanaerobacter ethanolicus*. Int J Syst Bacteriol 43:41-51.

Larsen L, Nielsen P, Ahring B K. (1997) *Thermoanaerobacter mathranii* sp. nov., an ethanol-producing, extremely thermophilic anaerobic bacterium from a hot spring in Iceland. Arch Microbiol 168:114-119.

Hungate R E. (1969) A roll tube method for cultivation of strict anaerobes. In: Methods in Microbiology Eds. Norris J R and Ribbons D W. pp 118-132. New York: Academic Press.

Chenna R, Sugawara H, Koike T, Lopez R, Gibson T J, Higgins D G, Thompson J D. (2003) Multiple sequence alignment with the Clustal series of programs. Nucleic Acids Res. 13:3497-3500.

Kumar S, Tamura K, Jakobsen I B, Nei M. (2001) MEGA2: molecular evolutionary genetics analysis software. Bioinformatics. 17:1244-1245.

U.S. Pat. No. 6,555,350

International patent application WO 2007/134607

What is claimed is:

1. A method of producing lactic acid or a salt or an ester thereof, the method comprising incubating lignocellulosic hydrolysates in the presence of cells of an isolated strain of *Thermoanaerobactor* at a temperature above 70 degrees Celsius, wherein the *Thermoanaerobactor* comprises a 16S rDNA sequence, wherein the 16S rDNA sequence comprises a nucleic acid sequence selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, and SEQ ID NO. 8.

2. The method of claim 1, wherein the lignocellulosic hydrolysates are obtained by providing a lignocellulosic biomass and subjecting the biomass to a treatment that separates the biomass into cellulose, hemicellulose and lignin.

3. The method of claim 2, wherein the biomass is a grass, optionally selected from the group consisting of switch grass, cord grass, rye grass, reed canary grass, mixed prairie grass, and *miscanthus*.

4. The method of claim 2, wherein the biomass is a straw, optionally selected from the group consisting of sugarcane straw, rice straw, barley straw, cereal straw, wheat straw, canola straw, and oat straw.

5. The method of claim 2, wherein the biomass is selected from the group consisting of agricultural waste, corn cobs, oat hulls, corn fiber, stover, soybean stover, corn stover, cotton stalks, forestry wastes, recycled wood pulp fiber, paper sludge, sawdust, sugar-methoding residues, sugarcane bagasse, and rice hulls.

6. The method of claim 2, wherein the biomass is a hardwood or a softwood.

7. The method of claim 2, wherein the treatment is selected from the group consisting of a mechanical treatment, a thermochemical treatment, and a biochemical treatment.

8. The method of claim 7, wherein the treatment is mechanical comminution, the method further comprising performing a subsequent treatment with sulfurous acid or its anhydride under increased heat and pressure, optionally with a sudden release of pressure.

9. The method of claim 7, wherein the treatment is mechanical comminution, the method further comprising performing a subsequent treatment with a chemical under increased heat and pressure, optionally with a sudden release of pressure, wherein the chemical is selected from the group consisting of sodium hydroxide, ammonium hydroxide, calcium hydroxide, and potassium hydroxide.

10. The method of claim 7, wherein the treatment is the mechanical comminution, the method further comprising steaming the biomass, separating partially and fully solubilized components from insoluble components, and providing the insoluble components as the lignocellulosic hydrolysates.

11. The method of claim 2, wherein the treatment is a steam treatment.

12. The method of claim 11, wherein the steam treatment comprises sulfurous acid, the treatment further comprising an enzymatic treatment.

13. The method of claim 12, wherein the enzymatic treatment comprises treatment with a cellulase, a glucosidase, and/or a hemicellulase.

14. The method of claim 1, wherein the strain is selected from the group consisting of DIB004G, DIB097G, DIB101G, DIB101X, DIB087G, DIB103X, DIB104X and DIB107X, wherein: DIB004G is DSMZ Accession No. 25179, DIB097G is DSMZ Accession No. 25308, DIB101G is DSMZ Accession No. 25180, DIB101X is DSMZ Accession No. 25181, DIB087G is DSMZ Accession No. 25777, DIB103X is DSMZ Accession No. 25776, DIB104X is DSMZ Accession No. 25778, and DIB107X is DSMZ Accession No. 25779.

15. The method of claim 14 wherein the strain is DIB004G (DSMZ Accession No. 25179).

16. The method of claim 1, wherein the 16S rDNA sequence is SEQ ID NO. 1.

* * * * *

SEQUENCE LISTING

<160> NUMBER OF SEQ ID NOS: 10

<210> SEQ ID NO 1
<211> LENGTH: 1422
<212> TYPE: DNA
<213> ORGANISM: Artificial Sequence
<220> FEATURE:
<223> OTHER INFORMATION: Thermoanaerobacter sp. DIB004G

<400> SEQUENCE: 1
ggttgggtca ccggcttcgg gtgtcgcagg ctctcgtggt gtgacgggcg gtgtgtacaa      60
ggcccgggaa cgtattcacc gcggcatgct gatccgcgat tactagcgat tccgacttca     120
tgcaggcgag ttgcagcctg caatccgaac ttggaccggc tttttgggat tcgctccgcc     180

```
tcacggcttc gcttccctct gtaccggcca ttgtagcacg tgtgtggccc agggcattta      240
gggcatgatg atttgacgtc atccccacct tcctccgtgt cctccacggc agtccctcta      300
gagtgcccgg cttaccegct ggcaactaga ggcaggggtt gcgctcgttg cgggacttaa      360
cccaacatct cacgacacga gctgacgaca accatgcacc acctgtgcag gctccttacc      420
tcccggtaag gtcgctcccc tttcggttcg ctactacctg catgtcaagc cctggtaagg      480
ttcttcgcgt tgcttcgaat taaaccacat gctccaccgc ttgtgcgggc cccgtcaat      540 tcctttgagt ttcaaccttg cggccgtact ccccaggcgg gtacttatt gcgttcgcta      600 cggcacggaa cgcttccgcg ccccacacct agtaccatc gtttacgcg tggactacca      660 gggtatctaa tcctgttcgc tccccacgct ttcgcgcctc agcgtcaggg ccagtccaga      720
gagtcgcctt cgccactggt attcctcccg atatctacgc atttcaccgc tacaccggga      780
attccactcc cctctcctgc cctctagcca atcagtttca gatgctaccc cccggttgag      840
cccgggtctt ttacacctga cttgattgac cgcctacgcg ccctttacgc ccagtaattc      900
cggacaacgc tcgcccccta cgtcttaccg cggctgctgg cacgtagtta gccggggctt      960
tcgtgtggta ccgtcatccc ttcttcccac actaacgggg tttacaaccc gaaggccttc     1020
ctcccccacg cggcgtcgct gggtcaggct tccgcccatt gcccaagatt ccccactgct     1080
gcctcccgta ggagtctggg ccgtgtctca gtcccagtgt ggccgtccac cctctcaggc     1140
cggctacccg tcgtcgcctt ggtaggccgt taccctacca actagctgat gggacgcggg     1200
cccatcctta agcggtagct tgcgcttccc tttcctccct ataggatgcc ctataaggag     1260
cttatccagt attaccaccc ctttcgaggt gctatcccgg tcttaagggt aggttgccca     1320
cgcgttactc acccgtccgc cgctatccgc cacccaacta cgttgagtgc cggaccgctc     1380
gactgcatgt gttaggcacg ccgccagcgt tcgtcctgag cc                        1422

<210> SEQ ID NO 2
<211> LENGTH: 1659
<212> TYPE: DNA
<213> ORGANISM: Artificial Sequence
<220> FEATURE:
<223> OTHER INFORMATION: Thermoanaerobacter sp. DIB087G

<400> SEQUENCE: 2
actcaagtgg gcacgttttt ttctcttcat cacgtttcta acatgcccac ttgagtgccg       60
ggttgggtca ccggcttcgg gtgttgcaga ctctcgtggt gtgacgggcg gtgtgtacaa      120
ggcccgggaa cgtattcacc gcggcatgct gatccgcgat tactagcgat tccgacttca      180
tgcaggcgag ttgcagcctg caatccgaac ttggaccggc ttttgggt ccgctccaga       240 tcgctccttc gcctccctct gtaccggcca ttgtagcacg tgtgtggccc agggcatata      300
gggcatgatg atttgacgtc atccccacct tcctccgtgt tgtccacggc agtccctcta      360
gagtgcctcc gtcactcaac tgaacacgct atcccttcct ctctactctt tcctaacatg      420
ttcagttgag tgacggactg gcaactagaa gcaagggttg cgctcgttgc gggacttaac      480
ccaacatctc acgacacgag ctgacgacaa ccatgcacca cctgtgcagg ctcccggcac      540
tcaagtaggc acttcattct ccctcttact accttctcta tcatgcccac ttgagtgccg      600
ggtcgctcac ctttcggctc gctactacct gcatgtcaag cctggtaag gttcttcgcg      660 ttgcttcgaa ttaaaccaca tgctccaccg cttgtgcggg ccccgtcaa ttcctttgag      720 tttcaacctt gcggccgtac tccccaggcg gggtacttat tgcgttaact acggcacgga     780
```

```
atgcttccgc atcccacacc tagtacccat cgtttacggc gtggactacc agggtatcta      840
atcctgtttg ctccccacgc tttcgcgcct cagcgtcagg gtcagtccag agagtcgcct      900
tcgccactgg tattcctccc gatatctacg catttcaccg ctacaccggg aattccactc      960
ccctctcctg ccctctagcc acccagtttc atgtgcatcc cccggggttga gcccgggttt    1020
tttacacctg acttaagtgg ccgcctacgc gcccttacg cccagtaatt ccggacaacg      1080
ctcgcccct acgtcttacc gcggctgctg cacgtagtt agccggggct ttcgtgtggt       1140
accgtcatct attcttccca cactatcgag ctttacgacc cgaaggcctt cttcgctcac    1200
gcggcgtcgc tgcgtcaggc tttcgcccat tgcgcaagat tccccactgc tgcctcccgt    1260
aggagtctgg gccgtgtctc agtcccagtg tggccgacca ccctctcagg ccggctaccc    1320
gtcgtcgcct tggtaggccg ttaccctacc aactagctga tgggacgcgg gcccatcctt    1380
aagcggtagc ttccgctacc ttccctcctc ataggatgcc ctacaaggag cttatccagt    1440
attagcaccc ctttcgaggt gttatcccgg tcttaagggt aggttgccca cgcgttactc    1500
acccgtccgc cgctatccgg cactcaactc cgtgcttacc ttactttgca ccacttttat    1560
tactttcttc ttctactata cttccttccc cttaagtaag cacttagttg agtgccggac    1620
cgctcgactt gcatgtgtta ggcacgccgc cagcgttcg                            1659

<210> SEQ ID NO 3
<211> LENGTH: 1436
<212> TYPE: DNA
<213> ORGANISM: Artificial Sequence
<220> FEATURE:
<223> OTHER INFORMATION: Thermoanaerobacter sp. DIB097X

<400> SEQUENCE: 3
cccggttggg tcaccggctt cgggtgtcgc aggctctcgt ggtgtgacgg gcggtgtgta       60
caaggcccgg gaacgtattc accgcggcat gctgatccgc gattactagc gattccgact      120
tcatgcaggc gagttgcagc ctgcaatccg aacttggacc ggcttttggg gattcgctcc      180
gcctcgcggc ttcgctcccc tctgtaccgg ccattgtagc acgtgtgtgg cccagggcat      240
atagggcatg atgatttgac gtcatcccca ccttcctccg tgtcctccac ggcagtcccc      300
ctagagtgcc cggcttaccc gctggcaact agaggcaggg gttgcgctcg ttgcgggact      360
taacccaaca tctcacgaca cgagctgacg acaaccatgc accacctgtg caggctcctt      420
acctcccggt aaggtcgctc ccctttcggt tcgctactac ctgcatgtca agccctggta      480
aggttcttcg cgttgcttcg aattaaacca catgctccac cgcttgtgcg gcccccgtc       540
aattcctttg agtttcaacc ttgcggccgt actccccagg cggggtactt attgcgttcg      600
ctacggcacg gaacgcttcc gcgcccacac cctagtaccc atcgtttaca gcgtggacta      660
ccagggtatc taatcctgtt cgctccccac gctttcgcgc tcagcgtca gggccagtcc      720
agagagtcgc cttcgccact ggtattcctc ccgatatcta cgcatttcac cgctacaccg      780
ggaattccac tcccctctcc tgccctctag ccaatcagtt tcagatgcta ccccggggtt      840
gagcccgggt cttttacacc tgacttgatt gaccgcctac gcgcccttta cgcccagtaa      900
ttccggacaa cgctcgcccc ctacgtctta ccgcggctgc tggcacgtag ttagccgggg      960
ctttcgtgtg gtaccgtcat cccttcttcc cacactaacg gggtttacaa cccgaaggcc    1020
ttcctccccc acgggcgtc gctgggtcag gcttccgccc attgcccaag attcccact      1080
gctgcctccc gtaggagtct gggccgtgtc tcagtcccag tgtggccgac caccctctca    1140
ggccggctac ccgtcgtcgc cttggtaggc cgttacccta ccaactagct gatgggacgc    1200
```

```
gggcccatcc ttaagcggta gcttgcgcct ccctttcctc cctataggat gccctataag    1260
gagcttatcc agtattacca ccccctttcga ggtgctatcc cggtcttaag ggtaggttgc    1320
ccacgcgtta ctcacccgtc cgccgctatc cgccacccaa ctacgttgag tgccggaccg    1380
ctcgacttgc atgtgttagg cacgccgcca gcgttcgtcc tgagccatga tcaaac        1436
```

<210> SEQ ID NO 4
<211> LENGTH: 1080
<212> TYPE: DNA
<213> ORGANISM: Artificial Sequence
<220> FEATURE:
<223> OTHER INFORMATION: Thermoanaerobacter sp. DIB101G

<400> SEQUENCE: 4

```
gctcaggacg aacgctggcg gcgtgcctaa cacatgcaag tcgagcggtc cggcactcaa      60
ctaagtgctt acttaagggg aaggaagtat agtagaagaa gaaggtaata aaagtgatgc     120
aaagtaaggt aagcacggag ttgagtgccg gatagcggcg gacgggtgag taacgcgtgg     180
gcaacctacc cttaagaccg ggataacacc tcgaaagggg tgctaatact ggataagctc     240
cttgtagggc atcctatgag gagggaaggt agcggaagct accgcttaag gatgggcccg     300
cgtcccatca gctagttggt agggtaacgg cctaccaagg cgacgacggg tagccggcct     360
gagagggtgg tcggccacac tgggactgag acacggccca gactcctacg ggaggcagca     420
gtggggaatc ttgcgcaatg ggcgaaagcc tgacgcagcg acgccgcgtg agcgaagaag     480
gccttcgggt cgtaaagctc gatagtgtgg gaagaataga tgacggtacc acacgaaagc     540
cccggctaac tacgtgccag cagccgcggt aagacgtagg gggcgagcgt tgtccggaat     600
tactgggcgt aaagggcgcg taggcggcca cttaagtcag gtgtaaaaaa cccgggctca     660
acccggggga tgcacatgaa actgggtggc tagagggcag gagaggggag tggaattccc     720
ggtgtagcgg tgaaatgcgt agatatcggg aggaatacca gtggcgaagg cgactctctg     780
gactgaccct gacgctgagg cgcgaaagcg tggggagcaa acaggattag ataccctggt     840
agtccacgcc gtaaacgatg gtactaggtg tgggatgcg gaagcattcc gtgccgtagt      900
taacgcaata agtaccccgc ctggggagta cggccgcaag gttgaaactc aaaggaattg     960 acggggggccc gcacaagcgg tggagcatgt ggtttaattc gaagcaacgc gaagaacctt    1020
accagggctt gacatgcagg tagtagcgag ccgaaaggtg agcgacccgg cactcaagtg    1080
```

<210> SEQ ID NO 5
<211> LENGTH: 1451
<212> TYPE: DNA
<213> ORGANISM: Artificial Sequence
<220> FEATURE:
<223> OTHER INFORMATION: Thermoanaerobacter sp. DIB101X

<400> SEQUENCE: 5

```
gccccacttt cgacggctcc ctccttcccg gttgggtcac cggcttcggg tgtcgcaggc      60
tctcgtggtg tgacgggcgg tgtgtacaag gcccgggaac gtattcaccg cggcatgctg     120
atccgcgatt actagcgatt ccgacttcat gcaggcgagt tgcagcctgc aatccgaact     180
tggaccggct ttttgggatt cgctccgcct cgcggcttcg cttccctctg taccggccat     240
tgtagcacgt gtgtggccca gggcatatag gcatgatga tttgacgtca tccccacctt     300
cctccgtgtc ctccacggca gtccctctag agtgccggc ttaccgctg caactagag       360 gcaggggttg cgctcgttgc gggacttaac ccaacatctc acgacacgag ctgacgacaa     420
```

| | |
|---|---:|
| ccatgcacca cctgtgcagg ctccttacct cccggtaagg tcgctcccct ttcggttcgc | 480 |
| tactacctgc atgtcaagcc ctggtaaggt tcttcgcgtt gcttcgaatt aaaccacatg | 540 |
| ctccaccgct tgtgcgggcc cccgtcaatt cctttgagtt tcaaccttgc ggccgtactc | 600 |
| cccaggcggg gtacttattg cgttcgctac ggcacggaac gcttccgcgc ccacaccta | 660 |
| gtacccatcg tttacagcgt ggactaccag ggtatctaat cctgttcgct ccccacgctt | 720 |
| tcgcgcctca gcgtcagggc cagtccgaga agtcgcctc gccactggta ttcctcccga | 780 |
| tatctacgca tttcaccgct acaccgggaa ttccactccc ctctcctgcc ctctagccaa | 840 |
| tcagtttcag atgctacccc cgggttgagc ccgggtcttt tacacctgac ttgattgacc | 900 |
| gcctacgcgc cctttacgcc cagtaattcc ggacaacgct cgcccctac gtcttaccgc | 960 |
| ggctgctggc acgtagttag ccggggcttt cgtgtggtac cgtcatccct tcttcccaca | 1020 |
| ctaacggggt ttacaacccg aaggccttcc tcccccacgc ggcgtcgctg ggtcaggctt | 1080 |
| ccgcccattg cccaagattc cccactgctg cctcccgtag gagtctgggc cgtgtctcag | 1140 |
| tcccagtgtg gccgaccacc ctctcaggcc ggctacccgt cgtcgccttg gtaggccgtt | 1200 |
| accctaccaa ctagctgatg ggacgcgggc ccatccttaa gcggtagctt gcgcctccct | 1260 |
| ttcctcccta taggatgccc tataaggagc ttatccagta ttaccacccc tttcgaggtg | 1320 |
| ctatcccggt cttaagggta ggttgcccac gcgttactca cccgtccgcc gctatccgcc | 1380 |
| acccaactac gttgagtgcc ggaccgctcg acttgcatgt gttaggcacg ccgccagcgt | 1440 |
| tcgtcctgag c | 1451 |

<210> SEQ ID NO 6
<211> LENGTH: 1465
<212> TYPE: DNA
<213> ORGANISM: Artificial Sequence
<220> FEATURE:
<223> OTHER INFORMATION: Thermoanaerobacter sp. DIB103X

<400> SEQUENCE: 6

| | |
|---|---:|
| ttcaccccaa tcacctgccc caccttcgac ggctccctcc tccccggttg ggtcaccggc | 60 |
| ttcgggtgtc gcaggctctc gtggtgtgac gggcggtgtg tacaaggccc gggaacgtat | 120 |
| tcaccgcggc atgctgatcc gcgattacta gcgattccga cttcatgcag gcgagttgca | 180 |
| gcctgcaatc cgaacttgga ccggcttttt gggattcgct ccgcctcgcg gcttcgctcc | 240 |
| cctctgtacc ggccattgta gcacgtgtgt ggcccagggc atatagggca tgatgatttg | 300 |
| acgtcatccc caccttcctc cgtgtcctcc acggcagtcc cctagagtg cccggcttac | 360 |
| ccgctggcaa ctagaggcag gggttgcgct cgttgcggga cttaacccaa catctcacga | 420 |
| cacgagctga cgacaaccat gcaccacctg tgcaggctcc ttacctcccg gtaaggtcgc | 480 |
| tcccctttcg gttcgctact acctgcatgt caagccctgg taaggttctt cgcgttgctt | 540 |
| cgaattaaac cacatgctcc accgcttgtg cgggccccg tcaattcctt tgagtttcaa | 600 |
| ccttgcggcc gtactcccca ggcggggtac ttattgcgtt cgctacggca cggaacgctt | 660 |
| ccgcgcccca cacctagtac ccatcgttta cagcgtggac taccagggta tctaatcctg | 720 |
| ttcgctcccc acgctttcgc gcctcagcgt cagggcagt ccagagagtc gccttcgcca | 780 |
| ctggtattcc tcccgatatc tacgcatttc accgctacac cgggaattcc actcccctct | 840 |
| cctgccctct agccaatcag tttcagatgc tacccccggg ttgagccgg tcttttaca | 900 |
| cctgacttga ttgaccgcct acgcgccctt tacgcccagt aattccggac aacgctcgcc | 960 |
| ccctacgtct taccgcggct gctggcacgt agttagccgg ggctttcgtg tggtaccgtc | 1020 |

```
atcccttctt cccacactaa cggggtttac aacccgaagg ccttcctccc ccacgcggcg      1080
tcgctgggtc aggcttccgc ccattgccca agattcccca ctgctgcctc ccgtaggagt      1140
ctgggccgtg tctcagtccc agtgtggccg accaccctct caggccggct acccgtcgtc      1200
gccttggtag gccgttaccc taccaactag ctgatgggac gcgggcccat ccttaagcgg      1260
tagcttgcgc ctccctttcc tccctatagg atgccctata aggagcttat ccagtattac      1320
cacccctttc gaggtgctat cccggtctta agggtaggtt gcccacgcgt tactcacccg      1380
tccgccgcta tccgccaccc aactacgttg agtgccggac cgctcgactt gcatgtgtta      1440
ggcacgccgc cagcgttcgt cctga                                            1465

<210> SEQ ID NO 7
<211> LENGTH: 1665
<212> TYPE: DNA
<213> ORGANISM: Artificial Sequence
<220> FEATURE:
<223> OTHER INFORMATION: Thermoanaerobacter sp. DIB104X

<400> SEQUENCE: 7
actcaagtgg gcacgttttt ttctcttcat cacgtttcta acatgcccac ttgagtgccg        60
ggttgggtca ccggcttcgg gtgttgcaga ctctcgtggt gtgacgggcg gtgtgtacaa       120
ggcccgggaa cgtattcacc gcggcatgct gatccgcgat tactagcgat tccgacttca       180
tgcaggcgag ttgcagcctg caatccgaac ttggaccggc tttttgggt ccgctccaga       240 tcgctccttc gcctccctct gtaccggcca ttgtagcacg tgtgtggccc agggcatata       300
gggcatgatg atttgacgtc atccccacct tcctccgtgt tgtccacggc agtccctcta       360
gagtgcctcc gtcactcaac tgaacacgct atcccttcct ctctactctt tcctaacatg       420
ttcagttgag tgacggactg gcaactagaa gcaagggttg cgctcgttgc gggacttaac       480
ccaacatctc acgacacgag ctgacgacaa ccatgcacca cctgtgcagg ctcccggcac       540
tcaagtaggc acttcattct ccctcttact accttctcta tcatgcccac ttgagtgccg       600
ggtcgctcac ctttcggctc gctactacct gcatgtcaag ccctggtaag gttcttcgcg       660
ttgcttcgaa ttaaaccaca tgctccaccg cttgtgcggg ccccgtcaa ttccctttgag       720 tttcaacctt gcggccgtac tccccaggcg gggtacttat tgcgttaact acggcacgga       780
atgcttccgc atcccacacc tagtacccat cgtttacggc gtggactacc agggtatcta       840
atcctgtttg ctccccacgc tttcgcgcct cagcgtcagg gtcagtccag agagtcgcct       900
tcgccactgg tattcctccc gatatctacg catttcaccg ctacaccggg aattccactc       960
ccctctcctg ccctctagcc acccagtttc atgtgcatcc cccgggttga gcccgggttt      1020
tttacacctg acttaagtgg ccgcctacgc gcccttacg cccagtaatt ccggacaacg      1080
ctcgccccct acgtcttacc gcggctgctg gcacgtagtt agccggggct ttcgtgtggt      1140
accgtcatct attcttccca cactatcgag ctttacgacc cgaaggcctt cttcgctcac      1200
gcggcgtcgc tgcgtcaggc tttcgcccat tgcgcaagat tccccactgc tgcctcccgt      1260
aggagtctgg gccgtgtctc agtcccagtg tggccgacca ccctctcagg ccggctaccc      1320
gtcgtcgcct tggtaggccg ttaccctacc aactagctga tgggacgcgg gcccatcctt      1380
aagcggtagc ttcgctacc ttccctcctc ataggatgcc ctacaaggag cttatccagt      1440
attagcaccc ctttcgaggt gttatcccgg tcttaagggt aggttgccca cgcgttactc      1500
acccgtccgc cgctatccgg cactcaactc cgtgcttacc ttactttgca ccacttttat      1560
```

| tactttcttc ttctactata cttccttccc cttaagtaag cacttagttg agtgccggac | 1620 |
| cgctcgactt gcatgtgtta ggcacgccgc cagcgttcgt cctga | 1665 |

<210> SEQ ID NO 8
<211> LENGTH: 1105
<212> TYPE: DNA
<213> ORGANISM: Artificial Sequence
<220> FEATURE:
<223> OTHER INFORMATION: Thermoanaerobacter sp. DIB107X

<400> SEQUENCE: 8

| tcaggacgaa cgctggcggc gtgcctaaca catgcaagtc gagcggtccg gcactcaacg | 60 |
| tagttgagtg gcggatagcg gcggacgggt gagtaacgcg tgggcaacct acccttaaga | 120 |
| ccgggatagc acctcgaaag gggtggtaat actggataag ctccttatag gcatcctat | 180 |
| agggaggaaa gggaagcgca agctaccgct taaggatggg cccgcgtccc atcagctagt | 240 |
| tggtagggta acggcctacc aaggckacga cgggtagccg gcctgagagg gtggtcggcc | 300 |
| acactgggac tgagacacgg cccagactcc tacgggaggc agcagtgggg aatcttgggc | 360 |
| aatgggcgga agcctgaccc agcgacgccg cgtgggggag gaaggccttc gggttgtaaa | 420 |
| ccccgttagt gtgggaagaa gggatgacgg taccacacga aagccccggc taactacgtg | 480 |
| ccagcagccg cggtaagacg taggggggcga gcgttgtccg gaattactgg gcgtaaaggg | 540 |
| cgcgtaggcg gtcaatcaag tcaggtgtaa aagacccggg ctcaacccgg ggtagcacc | 600 |
| tgaaactggt tggctagagg gcaggagagg ggagtggaat tcccggtgta gcggtgaaat | 660 |
| gcgtagatat cgggaggaat accagtggcg aaggcgactc tctggactgg ccctgacgct | 720 |
| gaggcgcgaa agcgtgggga gcgaacagga ttagataccc tggtagtcca cgctgtaaac | 780 |
| gatgggtact aggtgtgggg cgcggaagcg ttccgtgccg tagcgaacgc aataagtacc | 840 |
| ccgcctgggg agtacggccg caaggttgaa actcaaagga attgacgggg cccgcacaa | 900 |
| gcggtggagc atgtggttta attcgaagca acgcgaagaa ccttaccagg gcttgacatg | 960 |
| caggtggtag cgaaccgaaa ggtgagcgac cttaccggga ggtaaggagc ctgcacaggt | 1020 |
| ggtgcatggt tgtcgtcagc tcgtgtcgtg agatgttggg ttaagtcccg caacgagcgc | 1080 |
| aacccctgcc tctagttgcc agcgg | 1105 |

<210> SEQ ID NO 9
<211> LENGTH: 20
<212> TYPE: DNA
<213> ORGANISM: Artificial Sequence
<220> FEATURE:
<223> OTHER INFORMATION: 27F forward primer

<400> SEQUENCE: 9

| agagtttgat cmtggctcag | 20 |

<210> SEQ ID NO 10
<211> LENGTH: 19
<212> TYPE: DNA
<213> ORGANISM: Artificial Sequence
<220> FEATURE:
<223> OTHER INFORMATION: 1492R reverse primer

<400> SEQUENCE: 10

| ggttaccttg ttacgactt | 19 |